(12) United States Patent
Sanders et al.

(10) Patent No.: US 9,056,023 B2
(45) Date of Patent: Jun. 16, 2015

(54) LIMB VOLUME ACCOMMODATION IN PEOPLE WITH LIMB AMPUTATION

(71) Applicant: University of Washington Through Its Center For Commercialization, Seattle, WA (US)

(72) Inventors: Joan Sanders, Sammamish, WA (US); Brian Otis, Seattle, WA (US); Katheryn Allyn, Seattle, WA (US); Brian Hafner, Seattle, WA (US); John Cagle, Everett, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 14/298,661

(22) Filed: Jun. 6, 2014

(65) Prior Publication Data
US 2014/0288669 A1    Sep. 25, 2014

Related U.S. Application Data

(62) Division of application No. 13/368,276, filed on Feb. 7, 2012, now Pat. No. 8,784,340.

(60) Provisional application No. 61/440,308, filed on Feb. 7, 2011.

(51) Int. Cl.
*A61F 2/78*    (2006.01)
*A61B 5/103*    (2006.01)
(Continued)

(52) U.S. Cl.
CPC ....... *A61F 2/7812* (2013.01); *A61F 2002/5092* (2013.01); *A61F 2002/689* (2013.01);
(Continued)

(58) Field of Classification Search
CPC ........... A61F 2002/7818; A61F 2/7812; A61F 2002/5092; A61F 2002/762–2002/769; A61F 2002/7825; A61F 2002/7837; A61F 2002/785; A61F 2002/802; A61F 2002/805; A61F 2/80; A61F 2/7843; A61B 5/0002
USPC .................................................. 600/587–595
See application file for complete search history.

(56) References Cited

U.S. PATENT DOCUMENTS

| 5,133,776 A | 7/1992 | Crowder |
| 5,610,966 A | 3/1997 | Martell et al. |

(Continued)

FOREIGN PATENT DOCUMENTS

| WO | WO 92/08175 A1 | 5/1992 |
| WO | WO 03/009787 A2 | 2/2003 |

(Continued)

OTHER PUBLICATIONS

Notification of Transmittal of the International Search Report and the Written Opinion of the International Searching Authority, or the Declaration and International Search Report and Written Opinion of the International Searching Authority for International Application No. PCT/US2012/024192 mailed on Aug. 17, 2012, 11 pages.

(Continued)

*Primary Examiner* — Adam J Eiseman
(74) *Attorney, Agent, or Firm* — Kilpatrick Townsend & Stockton, LLP

(57) ABSTRACT

A prosthetic sock monitoring system is disclosed. The sock monitoring system includes a storage device and a data collection unit. The data collection unit is operable to receive data from at least one sensor coupled to a prosthetic sock that is wearable by a patient, and store the received data in the storage device. A prosthetic sock is also disclosed. The sock comprises material shaped to fit over at least a portion of the residual limb of the patient and a thickness adapted for inserting the residual limb into the socket of the prosthesis while the sock is fitted over the residual limb. The sock also comprises one or more of a sock identification unit and a force sensing device.

23 Claims, 16 Drawing Sheets

(51) Int. Cl.
*A61B 5/117* (2006.01)
*G06Q 10/08* (2012.01)
*G06F 19/00* (2011.01)
*A61F 2/50* (2006.01)
*A61F 2/68* (2006.01)
*A61F 2/70* (2006.01)
*A61F 2/76* (2006.01)

(52) U.S. Cl.
CPC ..... *A61F2002/705* (2013.01); *A61F 2002/765* (2013.01); *G06Q 10/087* (2013.01); *G06F 19/3418* (2013.01); *A61F 2002/7635* (2013.01); *A61F 2002/7818* (2013.01)

(56) References Cited

U.S. PATENT DOCUMENTS

| | | | |
|---|---|---|---|
| 6,447,448 B1 | 9/2002 | Ishikawa et al. | |
| 6,964,688 B1 | 11/2005 | Kania | |
| 7,150,762 B2 | 12/2006 | Caspers | |
| 7,190,273 B2 | 3/2007 | Liao et al. | |
| 7,558,622 B2 | 7/2009 | Tran | |
| 7,594,935 B2 | 9/2009 | Warila | |
| 7,655,049 B2 | 2/2010 | Phillips | |
| 7,670,386 B2 | 3/2010 | Ezenwa | |
| 7,704,282 B2 | 4/2010 | Disilvestro et al. | |
| 7,733,224 B2 | 6/2010 | Tran | |
| 7,780,741 B2 | 8/2010 | Janusson et al. | |
| 8,007,543 B2 | 8/2011 | Martin | |
| 8,108,036 B2 | 1/2012 | Tran | |
| 8,951,211 B2 * | 2/2015 | Sanders et al. | 600/587 |
| 8,978,224 B2 * | 3/2015 | Hurley et al. | 29/407.1 |
| 2004/0024312 A1 | 2/2004 | Zheng | |
| 2004/0059432 A1 * | 3/2004 | Janusson et al. | 623/36 |
| 2004/0167638 A1 | 8/2004 | Caspers | |
| 2004/0250819 A1 | 12/2004 | Blair et al. | |
| 2005/0101693 A1 | 5/2005 | Arbogast et al. | |
| 2005/0125078 A1 * | 6/2005 | Br. Janusson et al. | 623/36 |
| 2005/0240283 A1 | 10/2005 | Kania | |
| 2006/0154642 A1 | 7/2006 | Scannell | |
| 2006/0173259 A1 | 8/2006 | Flaherty et al. | |
| 2007/0009732 A1 * | 1/2007 | Tsai et al. | 428/349 |
| 2007/0055383 A1 | 3/2007 | King | |
| 2007/0112285 A1 | 5/2007 | Dar et al. | |
| 2007/0162153 A1 | 7/2007 | Barnes et al. | |
| 2008/0004904 A1 | 1/2008 | Tran | |
| 2008/0243266 A1 | 10/2008 | Haynes et al. | |
| 2008/0294019 A1 | 11/2008 | Tran | |
| 2009/0012372 A1 | 1/2009 | Burnett et al. | |
| 2009/0132056 A1 | 5/2009 | Kania | |
| 2010/0036455 A1 * | 2/2010 | Sanders et al. | 607/48 |
| 2010/0191153 A1 | 7/2010 | Sanders et al. | |
| 2010/0245114 A1 * | 9/2010 | Celik-Butler et al. | 340/825.49 |
| 2010/0312361 A1 | 12/2010 | Martin | |
| 2011/0015498 A1 | 1/2011 | Mestrovic et al. | |
| 2012/0226197 A1 | 9/2012 | Sanders et al. | |
| 2013/0123940 A1 * | 5/2013 | Hurley et al. | 623/33 |
| 2013/0274896 A1 * | 10/2013 | Wang et al. | 623/36 |
| 2014/0135946 A1 * | 5/2014 | Hurley et al. | 623/33 |

FOREIGN PATENT DOCUMENTS

| | | |
|---|---|---|
| WO | WO 2004/086997 A1 | 10/2004 |
| WO | WO 2006/135857 A2 | 12/2006 |
| WO | WO 2007/027660 A2 | 3/2007 |
| WO | WO 2008/055229 A2 | 5/2008 |
| WO | WO 2012/109277 A2 | 8/2012 |

OTHER PUBLICATIONS

Non-Final Office Action for U.S. Appl. No. 13/368,276 mailed on Aug. 15, 2013, 9 pages.
Notice of Allowance for U.S. Appl. No. 13/368,276 mailed on Mar. 6, 2014, 7 pages.

\* cited by examiner

LIMB VOLUME ACCOMMODATION IN PEOPLE WITH LIMB AMPUTATION

CROSS-REFERENCES TO RELATED APPLICATIONS

The present application is a Divisional of U.S. Ser. No. 13/368,276 filed Feb. 7, 2012 (Allowed); which application claims the benefit under 35 USC §119(e) of U.S. Provisional Appln. No. 61/440,308 filed Feb. 7, 2011. The full disclosures which are incorporated herein by reference in their entirety for all purposes.

BACKGROUND

Individuals born with lower limb loss or those who have acquired such an amputation through injury, infection, or disease are traditionally fit with a prosthetic socket and limb so as to provide them with the opportunity to achieve independent ambulation. In order for a patient to successfully stand and ambulate with a prosthesis, the prosthetic socket must transfer the loads that are normally distributed through the skeletal system to the residual limb and its delicate soft tissues. A prosthetic socket must have an intimate fit with the residual limb in order to effectively and safely transfer these forces. However, no socket fit is perfect and residual limbs continually change shape over time as the residual limb matures and/or atrophies, which may occur over the course of the day, week, or month. Further, patients often experience daily fluctuations in residual limb volume that occur as fluid enters and leaves the residual limb.

Patients are often encouraged to use removable interface materials to accommodate the changing size of the residual limb and maintain an optimal fit. Those whose limbs change in volume during the day are commonly advised by their practitioners to add or remove prosthetic socks in order to effectively manage these changes. A practitioner might recommend that certain numbers and/or plies (i.e., thickness) of socks be added or removed at certain times of the day, before or after certain activities or other treatments (e.g., dialysis), or when discomfort or pain is experienced by the patient, depending on the presentation of the residual limb tissues and the nature of discomfort experienced.

Changing socks properly promotes healthy skin tissues by maintaining well-distributed pressures and shear stresses on the residual limb and encourages a stable gait by limiting the pistoning (i.e., rubbing between the limb and socket) of the prosthesis on the residual limb. However, frequent donning and doffing of the prosthesis is inconvenient and many patients may elect not to add or remove socks. Further, individuals with cognitive impairments or poor limb sensation often have difficulty choosing or determining when to make sock changes. Further yet, many patients often fail to remember to conduct prescribed sock changes and, even when they do remember to conduct prescribed sock changes, fail to document such sock changes. The documenting of sock changes provides important diagnostic information to the practitioner.

If residual limb volume is not properly accommodated through volume management strategies such as prosthetic sock use, then residual limb soft tissues may be put at risk for edema, breakdown, or other skin conditions, such as verrucous hyperplasia. These factors are believed to ultimately contribute to dissatisfaction, discomfort, inactivity, disuse/abandonment of the prosthesis, and/or infections that may, in extreme cases, require surgical intervention or re-amputation of a portion of the limb. Although the exact cause is not known, the incidence of skin breakdown ranges from 24% to 41%, suggesting it is a serious problem for many amputees.

A first barrier to progress in the prescription and clinical application of sock accommodation strategies is a scarcity of data from which to derive meaningful decisions and recommendations concerning sock usage. Existing techniques do not indicate if and how consistently amputee patients change socks to address volume management issues and, further, if changing socks improves users' comfort and satisfaction with the prosthesis. The root of the difficulty in obtaining such data is a technological one: no instrument exists for monitoring sock use, or for facilitating implementation of volume accommodation prescriptions.

A second barrier to reaching these goals is the absence of normative data. In order to derive meaningful clinical knowledge from the application of novel therapeutic solutions, observation and study of the target population under usual and customary circumstances is required. However, again, no instruments currently exist for observing and studying a target population under usual and customary circumstances with respect to sock usage.

A third barrier to reaching these goals is the meaningful translation of such knowledge into clinical practice. Since no instruments currently exist for observing and studying a target population with respect to sock usage, it follows that techniques have yet to be considered, much less developed, for exploiting such data.

Attempts to obtain and provide practitioners with information about prosthetic patients' participation in their free-living environments has resulted in the development of accelerometer-based monitoring devices and strain-gage monitoring devices that are intended to be worn on the patient or attached to a prosthesis.

Accelerometer-based devices have been used to measure "activity" by means of step counts. The information collected with accelerometer-based devices is collected perpetually, stored locally (i.e., on the unit), and then retrieved at a later date. A classification accuracy of 98% has been considered acceptable for accelerometer-based activity monitors described in the literature. They require limited power and measure steps across a range of walking speeds. However, step counts provide limited clinical information as to how the prosthesis is used or how the user manages limb volume change. Thus, prosthetic interventions designed to help manage limb volume change would be expected to show similar results to studies reported in the literature that have evaluated componentry designed to alter loading patterns (such as shock-absorbing pylons or microprocessor-controlled prosthetic knees). These studies have reported that there is no measured clinical effect to changes in interventions when step counts are used as an outcome. Further, as step monitors are sensitive, stand-alone devices, they must be properly oriented on the patient to collect accurate data, and they can be selectively removed by the patient. Failure to wear the device properly or regularly may result in incomplete or erroneous usage information.

Strain gage-based devices exist to measure prosthesis forces and might help provide insight into how the prosthesis is used, but current devices are limited to short term use (e.g., 7 hours). Thus, the existing solutions to collecting perpetual, clinically-relevant information in free-living environments are limited in their capability to measure characteristics of clinical interest to a rehabilitation team. Existing solutions do not align with the needs of an efficient practice and add to the overall time and expense of care provided.

Accordingly, existing techniques fail to indicate how prosthetic users should manage their volume fluctuations with prosthetic socks or how sock usage affects prosthetic fit and comfort. Existing techniques also fail to indicate whether individuals, in their daily lives, follow clinical recommendations for accommodation and whether compliance affects their health and comfort.

BRIEF SUMMARY

Methods, systems and structures are provided for monitoring prosthetic sock usage or activity. A wireless sock monitor operates in a prosthesis for a period of time. In some embodiments, the wireless sock monitor operates continuously in a prosthesis for a period of at least one month. The wireless sock monitor may facilitate determinations of prosthetic sock usage patterns in persons, for example, with transtibial limb loss. Sock management strategies may be created based on objective sock monitor data, self-report data, and/or clinical input in an effort to enhance user comfort, satisfaction with the prosthesis, health, and/or function. In some embodiments, a feedback sock monitor system communicates a prescribed sock management strategy to a patient via, e.g., smartphone text messages and/or auditory/visual alarms. In other embodiments, the feedback sock monitor system may communicate sock use status to an actuator to adjust one or more properties (e.g., mechanical) of the prosthesis.

In some embodiments, the sock monitor method or system uses radio frequency identification and/or micro-fabrication technology. A very small unobtrusive sensor may be embedded within each prosthetic sock that sends information wirelessly about sock presence and sock-to-limb pressures to a small data processing and storage unit mounted to the pylori of the prosthesis or molded into the socket itself. In some embodiments, the sensor may monitor when and how often the prosthesis is worn, what socks are worn, when sock changes are made, and when and how long the patient rests, stands, and ambulates. The monitoring system facilitates the evaluation of self-selected use of prosthetic socks for the management of residual limb volume and comfort. In some embodiments, collected data on sock use patterns may be evaluated to determine patient activity, comfort, and/or adverse events (e.g., skin breakdown). Then collected data may then be used along with practitioner input to advise, recommend, and/or prescribe sock management strategies for patients. Developed management strategies may then be programmed into the monitor to create an "active" sock monitor system. The system may communicate to the patient via text messages and/or auditory/vibratory alarms when sock changes are recommended. In some embodiments, data is collected from practitioners and/or patients regarding the clinical efficacy of and/or satisfaction with the active sock monitoring system.

In some embodiments, the disclosed sock monitoring method, system or device may allow observation of a cohort of individuals who use socks to manage residual limb volume and do so in a way that does not interfere with their normal, habitual patterns. The use of preferred management strategies and the dissemination of information about such strategies may be immediately useful to scientists and clinicians seeking to develop improved limb management strategies for this patient population. Further, in some embodiments, such knowledge may be meaningfully translated into clinical practice. This transfer may be achieved through interactions with and the guidance of experienced, clinical experts using real patient models. To navigate this uncharted territory, in some embodiments, patients' volume management data is assessed to develop clinical recommendations for the observed patients with their regular practitioners, as they are most likely to understand the needs of these specific patients. In so doing, a paradigm of evidence-based practice is advanced where objective data is synthesized with clinical experience and patient values in an effort to develop comprehensive treatment solutions. The resulting management recommendations may then be programmed into the monitoring device and provide real-time feedback to the patients in an effort to improve clinical outcomes. In some embodiments, data collected from a number of patients may be added to a database to establish user practices, to which other researchers and practitioners may contribute using the disclosed sock monitor. This database may then serve as a foundation for comparative assessments to objectively and quantitatively assess if and how well intervention strategies (e.g., an active sock monitor) enhance patient outcomes such as comfort and satisfaction with the prosthesis. In some embodiments, this data may facilitate the development of individualized treatment strategies for patients that are supported with and substantiated by meaningful data.

In some embodiments, the sock monitor method, system, or device includes a software interface for patients and/or practitioners. In some embodiments, data management software includes a graphical user interface (GUI) to present volume management data to practitioners and/or patients. This software allows patients and/or practitioners to monitor prosthetic activity, visualize associated volume management strategies, and/or promote adherence to clinical recommendations. Results may be accessible by applications executable on electronic devices such as personal computers, smartphones, etc., for facilitating universal access.

The relevance of the proposed application to public health may include, among other benefits, new knowledge about sock usage in people with, for example, transtibial, transfemoral, transradial, and/or transhumeral limb loss, and a new technology to facilitate evidence-based care. Existing techniques fail to provide information regarding how sock usage affects comfort, satisfaction with the prosthesis, adverse events, and activity level of individuals with limb amputation. However, embodiments of the present invention may facilitate the design of sock usage strategies, and their prescription and implementation to people with, for example, transtibial amputation. Among other benefits, embodiments of the present invention may enhance the quality of life of people with limb loss. For example, embodiments of the present invention may enhance patient satisfaction, comfort, activity, and/or skin health.

Further, embodiments of the present invention may encourage changes in traditional clinical practice and facilitate improvements in the care of individuals with limb loss. Current prescription and management practices rely upon subjective feedback from patients. Embodiments of the present invention facilitate a shift toward evidence-based approaches to treating prosthetic patients and encourage the use of objective outcomes information to inform and guide clinical decisions. Such a transition is recognized as an immediate and present need in the field of amputee patient care.

DETAILED DESCRIPTION

Figure 1:
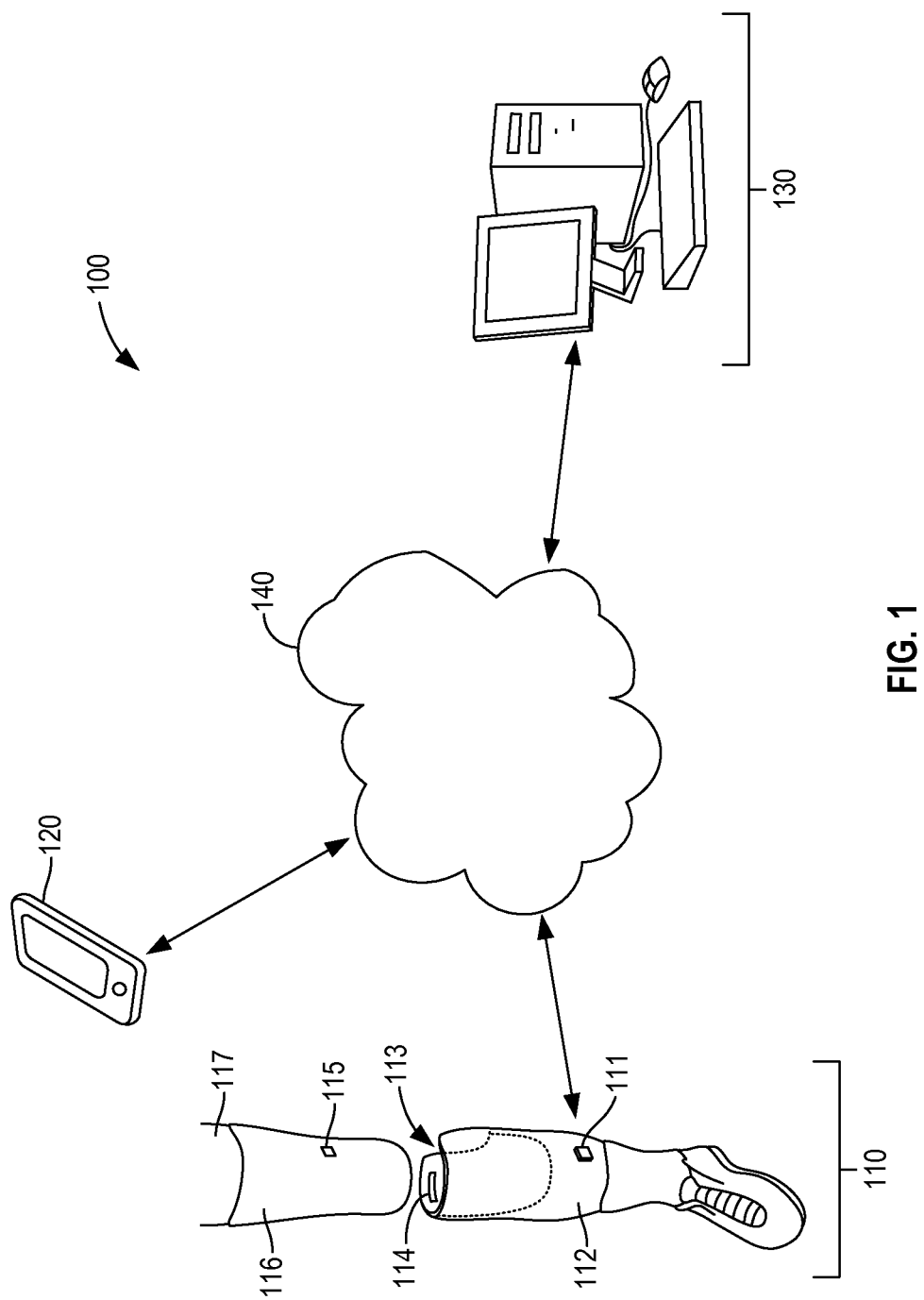
FIG. 1 illustrates a clinical interface system according to an embodiment of the present invention.

The selection of appropriate and timely rehabilitative interventions traditionally relies upon the experience of the clinician with input from the patient. This "experience-based" approach to amputee care may be visualized as a one-dimensional exchange of information that occurs between the practitioner and patient during regularly-scheduled clinical visits. The information obtained may include physical presentation of the patient, the results of clinical tests, and/or subjective responses to posed questions. These enable the practitioner to assess a patient's status, observe longitudinal changes, and then make treatment recommendations. This model is limited in that objective data are collected infrequently (i.e., only during scheduled visits) and may not represent real-world conditions (i.e., the free-living environment). This model is also predicated upon patient self-report and, as such, suffers from many of the same limitations as subjective survey instruments, such as generalization, comprehension, perception, honesty, and recall. These issues may be even more pronounced in a lower-limb amputee patient population that may experience cognitive impairment, for example, due to diabetes or peripheral arterial disease. Ultimately, these compounding issues promote a reactionary and iterative approach to amputee care that is inefficient, time consuming, and expensive.

An alternative to experienced-based care is an "evidence-based" solution where a practitioner develops a treatment plan through the use of best available evidence, sound clinical experience, and patients' goals and values. The intervention is then applied and clinical outcomes are later evaluated and revised, as necessary. Although this expanded approach to healthcare considers objective data (in the form of published research) in the derivation of the treatment plan, retrospective clinical assessment using traditional, in-clinic outcome measures is still subject to those same limitations (i.e., subjectivity, infrequency of assessment opportunities, compromised cognitive status of the patient) present in the described "experience-based" approach. As such, an improved means to objectively assess patients' outcomes during the provision of treatment interventions is needed. Information obtained continuously over the course of rehabilitation would have a direct impact on patient care as it would allow the managing practitioner to visualize the status, progress, and outcome of the patient and make informed (and timely) decisions based on the objective data now available to them. Further, patient information collected in this manner could be used to develop, change, and justify evidence-based therapies and interventions and ensure patients are receiving optimal care for their specific needs.

To address the need for objective information to support and facilitate evidence-based rehabilitation with patients with limb amputations, a clinical interface system may be used. The system may obtain critical, objective information directly from a data collection unit associated with a prosthesis worn by the patient and may make these data available to the practitioner and patient via a customizable software interface. Such a system may then allow for a multi-dimensional, bidirectional exchange of information between the patient, the practitioner, and/or the data collection unit. Such a system represents a paradigm shift in prosthetic healthcare and may offer numerous advantages over traditional experience and evidence-based approaches to prosthetic rehabilitation. For example, the practitioner may be able to access the device to obtain knowledge of the patient's historical or present status in his or her free-living environment and community, thereby augmenting the patient-reported experience with valid and reliable data (i.e., evidence) that is unencumbered with the limitations of subjective recall. For another example, the patient may be able to access the data collection unit to evaluate his or her performance against practitioner-established goals for a personalized and interactive rehabilitation program. For yet another example, the data collection unit may be able to monitor user performance for indications of adverse events, such as a change in prosthesis use, sock change patterns, and types of activity (e.g., standing, walking) and notify the practitioner and/or patient of altered behaviors. One of ordinary skill in the art will appreciate that other advantages may also be achieved. Ultimately, use of the clinical interface system and the provision of direct, real-time feedback to a patient (e.g., phone text messages, auditory/vibratory alarms) and an actuator device that controls mechanical qualities of the prosthesis (e.g., a fluid-insert system, a vacuum assist device, powered components such as knees, ankles, shanks, feet, etc.) may enable individualized treatment strategies and help to establish objective rationale for the prescription of specific prosthetic components intended to optimize a patient's function, health, safety, and/or quality of life.

The clinical applications for such a system are diverse. Disclosed herein is a distinct but nonexclusive configuration that is designed to address specific needs of a prosthetic rehabilitation team (e.g., a physician, therapist, and/or prosthetist). Although periodic (i.e., pre and post-intervention) assessment is standard practice in most rehabilitation services (including prosthetic care), the concept of long-term assessment of individuals with limb loss is less developed.

Turning now to the Figures, FIG. 1 illustrates a clinical interface system 100 according to an embodiment of the present invention. Clinical interface system 100 includes a prosthetic sock monitoring system 110 associated with a patient, a mobile computing device 120 associated with the patient, and a remote computing station 130 associated with a practitioner or other entity (e.g., a caregiver, the patient, etc.), all interconnected via a network 140.

Prosthetic sock monitoring system 110 includes a data collection unit 111 mechanically coupled to a prosthesis 112 wearable by the patient. Prosthesis 112 includes a socket 113 in which an antenna 114 is mounted. Prosthetic sock monitoring system 110 also includes at least one sensor 115 which is coupled to a prosthetic sock 116 that may be fitted over a residual limb 117 of the patient.

Prosthetic sock monitoring system 110 may be operable to perform one or more of a number of functions. In some embodiments, prosthetic sock monitoring system 110 may be operable to identify one or more characteristics of one or more prosthetic socks. For example, prosthetic sock monitoring system 110 may be operable to identify and determine whether the patient is wearing a particular prosthetic sock from a plurality of prosthetic socks, and when the patient is wearing the particular prosthetic sock. Prosthetic sock monitoring system 110 may be operable to identify and determine not only whether the patient is wearing a particular prosthetic sock, but may also be operable to identify a number of different prosthetic socks that the patient is simultaneously wearing. In some embodiments, prosthetic sock monitoring system 110 may be able to identify one or more characteristics of one or more prosthetic socks over a time frame. For example, prosthetic sock monitoring system 110 may be operable to identify when the patient wears particular prosthetic socks and for how long the patient wears the particular prosthetic socks.

Prosthetic sock monitoring system 110 may also be operable to identify one or more activities that the patient engages in. For example, prosthetic sock monitoring system 110 may be operable to identify and determine whether the patient is inactive, standing, or engaging in dynamic activity such as walking or running. In some embodiments, prosthetic sock monitoring system 110 may be operable to identify patient activities over a time frame. For example, prosthetic sock monitoring system 110 may be operable to identify when the patient runs and for how long the patient runs.

In some embodiments, prosthetic sock monitoring system 110 may be operable to communicate information to the patient. The information may be any suitable information for facilitating sock usage in accordance with a sock management strategy. A sock management strategy may identify, for example, which particular prosthetic socks or socks having particular characteristics the patient should wear and when the patient should wear such prosthetic socks. Prosthetic sock monitoring system 110 may be operable to communicate the information to the patient using one or more of a number of techniques. For example, auditory, visual, and/or tactile signals may be communicated to the patient via the data collection unit. For another example, auditory, visual, and/or tactile signals may be communicated to the patient via the mobile computing device 120.

In at least one embodiment, prosthetic sock monitoring system 110 may be operable to monitor a patient's compliance with a sock management strategy based on data received from at least one sensor. For example, data collection unit 111 (or another suitable device, such as mobile computing device 120 and/or remote computing station 130) may receive, from the at least one sensor 115, information indicative of sock usage. Data collection unit 111 may then be operable to compare that information with the sock management strategy to determine whether the patient is complying with the sock management strategy. If it is determined that the patient is complying with the strategy, the data collection unit 111 may continue to monitor for compliance. On the other hand, if it is determined that the patient is not complying with the strategy, the data collection unit 111 may communicate information to the patient or some other destination (e.g., a health care provider) indicating non-compliance and/or other suitable information for facilitating sock usage in accordance with the sock management strategy.

Prosthetic sock monitoring system 110 includes a data collection unit 111 operable to receive data from sensor 115 and store the received data in a storage device. In one embodiment, data collection unit 111 may receive and store the data from sensor 115 on a first periodic basis, and on a second periodic basis transmit the stored data to a remote computing device such as remote computing station 130 and/or mobile computing device 120. For example, once a second, multiple times a second, once a minute, once an hour, once a day, etc., data collection unit 111 may receive and store data from sensor 115. Then, once a week, multiple times a week, once a month, once every plurality of months, etc., data collection unit 111 may communicate the stored data to remote computing station 130. The data may be communicated via any suitable communication mechanism. For example, the data may be stored on a removable storage device which may then be coupled to remote computing station 130, or the data may be communicated via a wired connection between data collection unit 111 and remote computing station 130, or the data may be communicated via a network, such as network 140.

In some embodiments, data collection unit 111 may be mechanically coupled to prosthesis 112. Data collection unit 111 may be mechanically coupled to any suitable surface at any suitable location on prosthesis 112. For example, data collection unit 111 may be bonded to an interior or an exterior surface of socket 113. In one embodiment, data collection unit 111 may be bonded to an exterior surface of prosthesis 112 beside socket 113, while in another embodiment, data collection unit 111 may be bonded to an exterior surface of prosthesis 112 away from (e.g., below) socket 113. In at least one embodiment, data collection unit 111 may be coupled at or near a center of mass of prosthesis 112, thereby advantageously reducing interference with the inertial characteristics of the prosthesis. In other embodiments, data collection unit 111 is not mechanically coupled to prosthesis 112. For example, data collection unit 111 may be a portable device, such as a mobile computing device, that the patient may carry in, e.g., a pocket. For another example, data collection unit 111 may be mechanically coupled to something other than prosthesis 112. For example, data collection unit 111 may be mechanically coupled to a wrist band wearable by the patient, a necklace wearable by the patient, a belt wearable by the patient, etc.

Data collection unit 111 may be operable to acquire data from the at least one sensor 115 via one or more antennas 114.

Antenna 114 may be wired or wirelessly coupled to data collection unit 111. Antenna 114 may be provided in any one or more of a number of locations. For example, antenna 114 may be mechanically coupled to a surface of prosthesis 112, such as an exterior surface or an interior surface of prosthesis 112, or embedded within prosthesis 112. In one embodiment, antenna 114 is arranged on an interior or exterior surface of (or embedded in a material of) socket 113 of prosthesis 112. In some embodiments, antenna 114 may be included within data collection unit 111. For example, antenna 114 may be provided within data collection 111 such that, when data collection unit 111 is mechanically coupled to an exterior surface of prosthesis 112, antenna 114 is adjacent to the exterior surface of prosthesis 112.

Prosthesis 112 may be any suitable prosthetic limb or device used by a patient, such as a prosthetic arm, prosthetic leg, etc., and may be robotic, non-robotic, etc. Prosthesis 112 may be made of any suitable material, such as carbon fiber, plastic, polymer, glycol-modified polyethylene terephthalate, etc. Prosthesis 112 includes a socket 113, which is a cavity of prosthesis 112 shaped to receive a residual limb 117 of a patient. Socket 113 may have any suitable shape, such as a cone shape, a cylindrical shape, a spherical shape, etc., and may have any suitable size, ranging from small sizes suitable for fitting on children to large sizes suitable for fitting on adults. In at least one embodiment, prosthesis 112 may be alterable. That is, one or more characteristics of the prosthesis 112, such as a size, a fit, a socket stiffness, a foot or ankle portion, temperature, etc., may be altered. For example, the prosthesis may include fluid-filled inserts and/or a vacuum assist for altering a socket size. For another example, the prosthesis may include powered joints such as an ankle joint. For yet another example, the prosthesis may include a heating element for changing a temperature of the prosthesis or a residual limb disposed in the prosthesis. Accordingly, prosthesis 112 may also include one or more actuators for adjusting one or more properties of the prosthesis. For example, the actuator may be a motor, a vacuum, a heating element, etc.

Sensor 115 may be one or more sensors that are either separate from one another or integrated with one another. In one embodiment, sensor 115 is a sock identification unit operable to identify at least one characteristic of the prosthetic sock and communicate the at least one characteristic to a computing device separate from prosthetic sock 116, such as data collection unit 111. For example, the sock identification unit may be operable to provide a unique identifier associated with a particular sock. For another example, the sock identification unit may be operable to identify a characteristic such as a thickness of the prosthetic sock, material which the prosthetic sock is made, breathability of the prosthetic sock, elasticity of the prosthetic sock, size of the prosthetic sock, etc. In another embodiment, sensor 115 is a force sensing device operable to determine an amount of force applied to the force sensing device and communicate information indicating the amount of force applied to the force sensing device to a computing device separate from prosthetic sock 116, such as data collection unit 111. For example, sensor 115 may determine an amount of force applied by one or more residual limb 117 and prosthesis 112. While many embodiments described herein discuss sensor 115 as including one or more of a sock identification unit and a force sensing device, one of ordinary skill in the art would recognize that the sensor 115 may include one or more of a variety of different types of sensors, including, e.g., temperature sensors, electromyography sensors, limb fluid volume sensors (e.g., a bioimpedance sensor), accelerometer, tissue oxygenation sensor, displacement sensor (e.g., for measuring a distance between a sock and socket), angle sensor, etc. Further, one would recognize that multiple sensors, either the same or of a different type, may be provided within the same prosthetic sock and that, while shown as being separate from data collection unit 111, may be part of data collection 111, or have one or more portions that are part of data collection unit 111 (e.g., some sensors may be part of sensor 115, while other sensors may be part of data collection unit 111), or may be remote from prosthetic sock 116 and/or prosthesis 112 (e.g., a remote temperature sensor).

In some embodiments, sensor 115 may be operable to reduce its power requirements using any one or more of a number of techniques. For example, sensor 115 may include an energy harvesting element (e.g., a piezoelectric element) operable to power one or more elements of sensor 115, where the energy harvesting element may be operable to acquire energy from one or more of a number of different sources, such as movement of the patient, heating of the patient, impact of the patient or prosthesis with supporting surfaces, perspiration of the patient, etc. For another example, sensor 115 may implement duty cycling such that information is communicated from sensor 115 only at certain time intervals. For yet another example, sensor 115 may acquire power or a charge from one or more external devices, such as data collection unit 111. Further, multiple sensors may, in some embodiments, be coupled to one another using one or more of a number of techniques. For example, a thin flat conductive wire or thread may be sewn into prosthetic sock 116 to electrically couple two sensors together, such as a piezoresistive film (e.g., force sensor) and an RFID tag (e.g., sock identifier) . Further, the sensors may be coupled to an interior or exterior surface of prosthetic sock 116, and in one embodiment, one or more sensors may be located within prosthetic sock 116. For example, the sensors may be sewn between fabric layers of prosthetic sock 116. Such an arrangement may advantageously reduce discomfort levels and increase the resilience of the sensors to damage from wear and washing.

Prosthetic sock 116 may include any one or more materials shaped to fit over at least a portion of residual limb 117. For example, prosthetic sock 116 may include one or more of cotton, wool, synthetic fiber, nylon, gel, etc. Further, the material of prosthetic sock 116 may be shaped to fit over at least a portion of residual limb 117 and have a thickness adapted for inserting residual limb 117 into socket 113 while prosthetic sock 116 is fitted over the residual limb 117. For example, prosthetic sock 116 may have a cone shape, a cylindrical shape, a spherical shape, etc., and have a size such as 1-ply, 2-ply, 3-ply, 4-ply, 5-ply, 6-ply, a range from 1-ply to 6-ply, or greater than 6-ply or less than 1-ply. In many embodiments, prosthetic sock 116 is distinguished from an elastomeric liner (not shown), which is typically made of a silicon or urethane and which is a first layer disposed over a residual limb 117 in contact with residual limb 117. Accordingly, in many embodiments, prosthetic sock 116 is not directly in contact with residual limb 117, but rather is displaced from the exterior surface of residual limb 117 by a certain distance. For example, the elastomeric liner may have a thickness of 3 mm, 5 mm, 7 mm, 9 mm, or in a range from 3 mm to 9 mm, or less than 3 mm, or greater than 9 mm, and thus prosthetic sock 116 may be displaced from the exterior surface of residual limb 117 by a corresponding distance.

In some embodiments, sensor 115 may be embedded within prosthetic sock 116 or coupled to a surface of prosthetic sock 116. For example, sensor 115 may be sewn into the material of prosthetic sock 116. For another example, sensor 115 may be mechanically coupled to an exterior or interior surface of prosthetic sock 116. Further, sensor 115 may be provided at any one or more of a number of predetermined locations on or in prosthetic sock 116. For example, sensor 115 may be located at a brim of the material, an end of the material opposite an end having an opening for receiving residual limb 117 (i.e., an end opposite the brim), and/or at one or more locations between the brim and the end of the material opposite that for receiving residual limb 117. In some embodiments, a location of sensor 115 may be determined based on a location of antenna 114. For example, sensor 115 may be provided at a location on or in prosthetic sock 116 such that sensor 115 is located at a center of antenna 114 when prosthetic sock 116 is disposed over residual limb 117 and inserted into socket 113. In other embodiments, a location of sensor 115 may be determined based on load bearing sites of the prosthetic sock. For example, the anterior surface and the posterior surface may provide force information relevant to the fit and/or alignment of the prosthesis and thus sensor 115 should be provided at these locations.

Mobile computing device 120 may be any suitable electronic computing device for outputting information to the patient, and may be local to or remote from the patient. In some embodiments, mobile computing device 120 may display or otherwise output information communicated to it from another device. For example, mobile computing device 120 may display a text message in response to an instruction communicated from data collection unit and/or remote computing station 130. In other embodiments, mobile computing device 120 may execute instructions corresponding to a sock management strategy. For example, mobile computing device 120 may include information identifying a sock management strategy and, at certain times or instances specified by the sock management strategy, mobile computing device 120 may output information to the patient instructing the patient to, e.g., change prosthetic socks. Mobile computing device 120 may acquire information defining a particular sock management strategy associated with the patient from one or more of a number of sources. For example, a user such as the patient or a practitioner may program the information into the mobile computing device 120. For another example, mobile computing device 120 may download the information from a remote source such as remote computing station 130.

Figure 3:
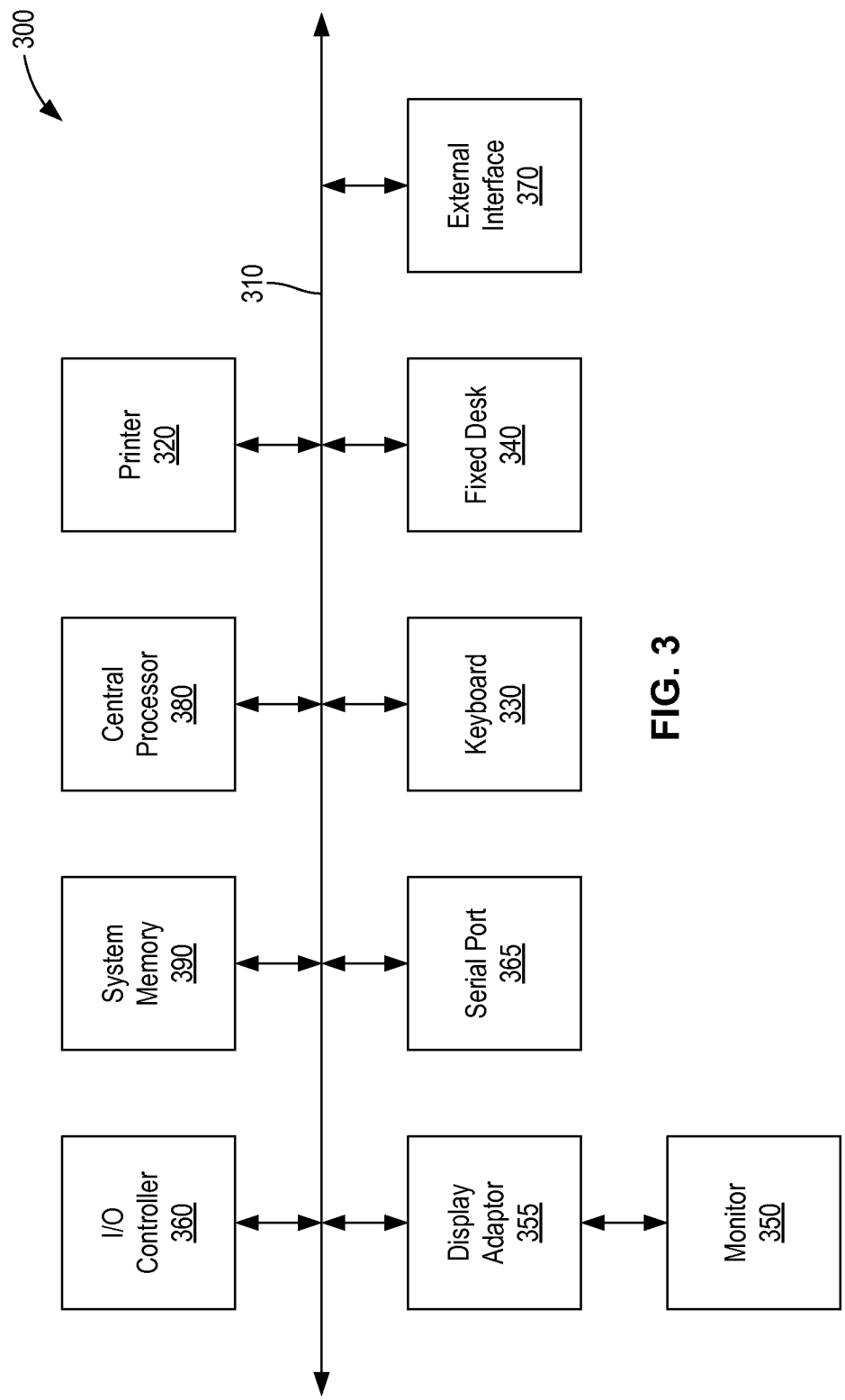
FIG. 3 is a diagram of a computer apparatus according to an example embodiment.

Turning briefly to FIG. 3, FIG. 3 is a diagram of a computer apparatus 300 according to an embodiment, where mobile computing device 120 may include one or more components of computer apparatus 300. For example, mobile computing device 120 may include an output device such as monitor 350 for displaying information communicated to mobile computing device 120 from, for example, data collection unit 111. In some embodiments, mobile computing device 120 may include a storage element such as fixed disk 340 and/or system memory 390, where the storage element is operable to receive information defining a sock management strategy. As previously mentioned, the information defining a sock management strategy may be received from one or more devices, such as remote computing station 130. Mobile computing device 120 may also include a processor, such as central processor 380, operable to perform various operations. For example, the processor may be operable to process the information defining the sock management strategy to determine when the patient should wear a particular prosthetic sock selected from a plurality of different prosthetic socks.

In some embodiments, mobile computing device 120 may also include an output device operable to provide an indication to the patient indicating when the patient should wear the particular prosthetic sock selected from the plurality of different prosthetic socks. The indication may be one or more of a variety of indicators, such as an auditory indicator, a visual indicator, a tactile indicator, etc. In at least one embodiment, mobile computing device 120 may include a communication unit, such as serial port 365 and/or external interface 370, operable to receive information communicated thereto from other devices such as data collection unit 111 and/or remote computing station 130. In some embodiments, the information communicated from data collection unit 111 may include information identifying at least one characteristic of a prosthetic sock currently being worn by the patient, and the processor may be operable to determine when the patient should wear a particular prosthetic sock based on the sock currently being worn by the patient. In other embodiments, the information communicated from data collection unit 111 may include information indicating the amount of force applied to a force sensing device coupled to a prosthetic sock currently being worn by the patient, and the processor may be operable to determine when the patient should wear a particular prosthetic sock based on the amount of force applied to the force sensing device.

In at least one embodiment, one or more instructions may be communicated to prosthesis 112 to instruct the prosthesis 112 to alter one or more of its characteristics (e.g., size, fit, socket stiffness, foot/ankle flexibility, alignment, etc.). The instruction may be sent by any suitable device, such as by data collection unit 111, mobile computing device 120, and/or remote computing station 130. In some embodiments, the instructions may be generated based on sensor information obtained by data collection unit 111. In other embodiments, the instructions may be generated based on a defined sock management strategy. In yet other embodiments, the instructions may be generated based on whether obtained sensor information indicates compliance with a defined sock management strategy.

Remote computing station 130 is a computing device associated with a practitioner remote from the patient, where the practitioner may be responsible for assisting one or more patients in managing use of prosthesis. Remote computing station 130 may be operable to receive data sensed and monitored by prosthetic sock monitoring system 110, and process the received data to generate a variety of information for the practitioner. In some embodiments, remote computing station 130 may be operable to generate information defining a sock management strategy that indicates when a patient associated with the prosthetic sock monitoring system 110 should wear a particular prosthetic sock selected from a plurality of different prosthetic socks. In accordance with at least one embodiment, prosthetic sock monitoring system 110 may be operable to acquire data from a plurality of prosthetic sock monitoring systems associated with different patients, and use such data to generate one or more sock management strategies for particular patients.

Turning briefly to FIG. 3, FIG. 3 is a diagram of a computer apparatus 300 according to an embodiment, where remote computing station 130 may include one or more components of computer apparatus 300. For example, remote computing station 130 may include an interface element such as serial port 365 and/or external interface 370 operable to facilitate communication with prosthetic sock monitoring system 110 and/or mobile computing device 120 and/or storage elements associated with one or more of prosthetic sock monitoring system 110 and mobile computing device 120, so as to receive various information regarding the monitoring of one or more sensors 115 and, in some embodiments, communicate information such as information defining a sock management strategy to one or more of prosthetic sock monitoring system 110 and mobile computing device 120. Remote computing station 130 may also include a processor such as central processor 380 that may be operable to, e.g., process received data as described herein. In some embodiments, remote computing station 130 may also include a display element such as monitor 350 for displaying various received and/or processed information as described herein.

In at least one embodiment, remote computing station 130 is operable to receive from prosthetic sock monitoring system 110, via, e.g., serial port 365 and/or external interface 370, one or more of: information indicating one or more characteristics of at least one prosthetic sock (e.g., prosthetic sock 116) worn by a patient associated with the prosthetic sock monitoring system 110 and indicating a time frame associated with the one or more characteristics, and information indicating an amount of force applied to a force sensing device coupled to a prosthetic sock (e.g., prosthetic sock 116) worn by a patient associated with the prosthetic sock monitoring system 110 (e.g., a force applied to a region of the prosthetic sock 116) and indicating a time frame associated with the amount of force applied to the force sensing device. Remote computing station 130 may then be operable to store the received data in a storage element such as fixed disk 340 and, in some embodiments, process the received data using, e.g., central processor 380, to generate sock usage data indicating the usage of one or more prosthetic socks by the patient over at least a portion of the time frame. Remote computing station 130 may also be operable to cause the generated sock usage data to be displayed on a display device such as monitor 350 or, in some embodiments, a display of mobile computing device 120.

In some embodiments, the information indicating one or more characteristics of the at least one prosthetic sock worn by the patient may be processed by remote computing station 130 to determine one or more of a variety of information. For example, the information may be processed to determine the number of prosthetic socks worn by the patient over different time intervals of the time frame, the timing of sock changes by the patient, the frequency of sock changes by the patient, an increase in sock thickness for sock changes by the patient, a decrease in sock thickness for sock changes by the patient, and/or a change of socks by the patient without any change in the sock thickness.

In other embodiments, the information indicating an amount of force applied to a force sensing device may be processed by remote computing station 130 to determine one or more of a variety of information. For example, the information may be processed to determine the timing of the patient's inactivity over the time frame, the duration of the patient's inactivity over the time frame, the timing of the patient's standing over the time frame, the duration of the patient's standing over the time frame, the timing of the patient's dynamic activity over the time frame, the timing at which the patient does not wear the prosthesis over the time frame, and/or the duration which the patient does not wear the prosthesis over the time frame. The patient's activity may be, for example, sitting, standing, ambulating, prosthesis donning, and/or prosthesis doffing. Further, in some embodiments, remote computing station 130 may process both the sock usage data and the information indicating the amount of force applied to the force sensing device to determine the number of prosthetic socks worn by the patient over different time intervals of the time frame while engaging in different activities.

In at least one embodiment, remote computing station 130 is operable to generate information defining a sock management strategy that indicates when a patient associated with the prosthetic sock monitoring system should wear a particular prosthetic sock selected from a plurality of different prosthetic socks. Central processor 380 of remote computing station 130, for example, may generate the sock management strategy based on one or more inputs provided to remote computing station 130. For example, the sock management strategy may be generated based on the sock usage data, the information indicating the amount of force applied to the force sensing device, and/or information indicating patient comfort level provided by the patient.

In some embodiments, remote computing station 130 may be operable to communicate, for example via serial port 365 and/or external interface 370, the information defining the sock management strategy to one or more devices associated with the patient, such as prosthetic sock monitoring system 110 and/or mobile computing device 120. In one embodiment, the information defining the sock management strategy may be operable to cause the device, e.g., mobile computing device 120, to instruct the patient when to wear a particular prosthetic sock selected from a plurality of different prosthetic socks.

As previously mentioned, remote computing station 130 may be operable to receive data from a plurality of devices associated with a plurality of different patients. For example, remote computing station 130 may receive, from a plurality of prosthetic sock monitoring systems each associated with a unique patient, one or more of: sock usage data and information indicating an amount of force applied to a force sensing device coupled to a prosthetic sock worn by the patient. In some embodiments, the information defining the sock management strategy for a particular patient may be generated from the data received from the plurality of prosthetic sock monitoring systems.

Network 140 is any suitable network for enabling communications between various entities, such as between prosthetic sock monitoring system 110, mobile computing device 120, and/or remote computing station 130. Such a network may include, for example, a local area network, a wide-area network, a virtual private network, the Internet, an intranet, an extranet, a public switched telephone network, an infrared network, a wireless network, a wireless data network, a cellular network, or any other such network or combination thereof. The network may, furthermore, incorporate any suitable network topology. Examples of suitable network topologies include, but are not limited to, simple point-to-point, star topology, self organizing peer-to-peer topologies, and combinations thereof. Components utilized for such a system may depend at least in part upon the type of network and/or environment selected. Network 140 may utilize any suitable protocol, such as TCP/IP, OSI, FTP, UPnP, NFS, CIFS, and AppleTalk. Communication over the network may be enabled by wired or wireless connections, and combinations thereof. In some embodiments, parts or all of network 140 may be replaced with direct wired or wireless connections between the devices. For example, in one embodiment, data collection unit 111 may be connected by a wire to mobile computing device 120 and/or remote computing station 130. In other embodiments, network 140 may be replaced with portable storage media. For example, data collection unit 111 may include a removable storage medium for storing information collected from the at least one sensor 115. The removable storage medium may then be directly or indirectly coupled to mobile computing device 120 and/or remote computing station 130 for communicating information between the devices.

In some embodiments, clinical interface system 100 may be implemented as part of a temporary treatment plan for a patient. For example, patients are asked to temporarily refrain from using (or relinquish) their usual and customary prosthetics socks, and are then provided with multiple sets of prosthetic socks including one or more devices (e.g., sensors) described herein. The new prosthetic socks may be identical to the patient's previous socks in design and shape, with the exception of the above inclusions. In some embodiments, each set of socks may consist of three 1, 2, and 4-ply socks. Before providing the socks to the patients, the thickness of each sock is measured using a custom instrument. In some embodiments, the instrument is a compression testing device with an inductive sensor embedded within the base to measure distance to the upper steel. In some embodiments, sock thickness is measured while the sock is under 60% strain and 30 kPa pressure, since these are typical use conditions for a patient that is either sitting or standing, while in other embodiments sock thickness may be measured while the sock is at 100 kPa pressure, which is typical for a patient that is walking. The sensors provided in each sock may, as discussed herein, uniquely identify each sock and in some embodiments provide force related information. In some embodiments, the patient's regular liner(s) may also be instrumented with the same type of force sensor as used for the socks to monitor activity, in the event the patient, at times, does not wear any socks. In some embodiments, the liner sensor is positioned on the posterior surface, a region typically of uniform local pressure. This sensor may be calibrated to the patient during the initial lab visit so as to establish relationships between sensor output and weight bearing.

Clinical interface system 100 may then monitor both sock presence and patient activity over a certain period of time, e.g., 4 weeks. All data may be stored by data collection unit 111, and downloaded to, e.g., remote computing station 130 at the end of the monitoring period. Each patient's comfort, incidence of skin problems, and medical visits may be assessed on a periodic, e.g., daily, basis via a daily cell phone text message, phone call, and/or email (e.g., whichever medium the patient chooses) sent by the research prosthetist. In some embodiments, the patient is queried using the Socket Comfort Score (SCS), a tool developed to assess prosthetic users' comfort with a prosthesis. The SCS may ask the question, "On a 0-10 scale, if 0 represents the most uncomfortable socket fit you can imagine, and 10 represents the most comfortable socket fit, how would you score the comfort of the socket fit of your artificial limb at the moment?" The presence of adverse skin conditions may also queried, "Are you experiencing unusual redness, soreness, or injury on your residual limb today?" Patients enter "yes" or "no" in response to this question. Patients may be asked if they attended a medical visit, such as dialysis, physical therapy, or prosthetic checkup. If patients respond in the affirmative, they may be asked to input the type and time of the visit. In the event patients do not respond to a text message, phone call, and/or email, they may be interviewed with a follow-up phone call. Collected data may be acquired securely and stored in a password-protected data file for subsequent analysis.

At the conclusion of the monitoring period, a practitioner may perform a thorough inspection of the patient's skin and note any signs of poor socket fit. Alternatively or additionally, patients may be asked to complete a short, 25-question survey which includes four subscales (i.e., ambulation, utility, residual limb health, and well-being) of the Prosthesis Evaluation Questionnaire (PEQ), a general health instrument designed to assess the user's prosthetic experience over the prior 4-week period. This survey may include at least one question related to patients' overall satisfaction with their prosthesis over the test period. All of this information may be collected at any suitable computing device, such as remote computing station 130, for processing.

The data received from data collection unit 111 (e.g., the data received from the one or more sensors 115), may be processed by any suitable computing device (e.g., mobile computing device 120 and/or remote computing station 130) to identify the timing and frequency of sock changes as well as the patient's activity during the day. The nature of the sock change may also be identified, for example: an increase in the sock thickness; a decrease in the sock thickness; or a change in socks without a change in thickness. The number of socks worn over time may also be tabulated. Timings and durations of inactivity, standing (static weight-bearing), and dynamic activity (non-static weight bearing) as well as durations the prosthesis is not worn may be determined through analysis of the force/pressure-time data. For example: (i) zero pressure on all sock and liner sensors: doffed prosthesis; (ii) constant low pressure: inactivity; (iii) constant moderate to high pressure: standing; and (iv) varying moderate to high pressure: dynamic activity. In some embodiments, a practitioner also visually inspects the sock monitor data for other clinically-relevant information, such as patterns of weekday vs. weekend sock use that may improve our communities' understanding of self-selected volume management strategies or inform clinical practice in this area.

Residual limb volume management strategies may then be developed, by any suitable computing device (e.g., mobile computing device 120 and/or remote computing station 130) for patients. The developed strategies may be programmed into the monitoring system (e.g., data collection unit 111 and/or mobile computing device 120) and patients may be offered options for receiving management recommendations (e.g., auditory signal, vibratory signal, and/or text message sent to the patient via, e.g., mobile computing device 120 and/or data collection unit 111).

The volume management data, activity data, perceived comfort, and incidence of adverse skin conditions collected may be shared with patients' prosthetists. In some embodiments, measures of central tendency (i.e., mean, median, and mode) and variability (i.e., standard errors/deviations) of observed sample data collected, the results of hypotheses testing (e.g., strong correlations among key variables), and individualized results for specific patients may be generated using one or more suitable computing devices (e.g., mobile computing device 120 and/or remote computing station 130). The information may then be communicated to a variety of people, such as a patient's prosthetist, who may then be asked, with input from the study investigators, to assist in developing a volume management strategy for each patient based on the presented information.

In addition to viewing the study results, each practitioner may be presented with their patient's sock usage data in a report format. Clinical use data highlights the most clinically relevant information, such as most commonly worn socks, the percentage of day/week/month in which each was worn, and a daily account of any sock changes. Socks, identified by their unique identifiers, may be shown so as to demonstrate the incremental addition or removal of socks. For example, if a patient begins the day with a 1-ply sock and then later adds a 1-ply sock and a 2-ply sock, all three concurrent socks worn are displayed (as opposed to just showing a 4-ply equivalent sock). Such information may be useful so that the practitioners can accommodate patients' habits and develop individualized treatment strategies that work best for each patient.

An example of a treatment strategy developed through the use of the data collected from data collection unit 111 may be as follows. A patient presents with fairly low (mean=5.4) comfort scores during the work week and higher (mean=7.9) comfort scores on weekends. The data collected from data collection unit 111 shows that, during the work week, the patient dons a 4-ply prosthetic sock in the morning, and does not change socks over the day. On weekends, the patient dons only a 2-ply sock in the morning, but then adds an additional 2-ply around mid-day and another 1-ply late in the afternoon. The practitioner and/or computer associated with the practitioner suspects that the patient slowly loses volume over the day, but during work days he overcompensates for anticipated volume loss most of the day and does not change socks because he gets preoccupied with work. The practitioner and/or computer associated with the practitioner elects to reinforce the weekend-like staged approach to sock changes and programs the monitor to recommend a 2-ply sock first thing in the morning, exchange it for a 4-ply at lunch, and then add a 1-ply sock before heading home. The data collection unit 111 and/or mobile computing device 120 may then be programmed with such a sock management strategy and subsequently operate to prompt the patient to change socks at the scheduled times, ideally improving the patient's overall comfort and skin health.

In some embodiments, the data collection unit 111 and/or mobile computing device 120 may be programmed with one or more of five sock management strategies. One skilled in the art will appreciate that additional or alternative sock management strategies may be employed. (1) Change socks at set times each day: the sock management strategy identifies the times of day for sock change, the number of socks, and ply of those socks to be worn. (2) Change socks based on activity levels and/or a history of activity levels (e.g., standing, walking, doffing) achieved during the day: the sock management strategy identifies the threshold activity levels for sock change, and the number and ply of socks to be worn. (3) Change socks based on a history of wearing a prosthesis during the day (e.g., if a prosthesis is not worn much during the day, then no recommendation to add socks). (4) Change socks differently on different days, depending on timing of intervention/therapy sessions (e.g. dialysis): the sock management strategy varies the number and ply of socks according to the patient's intervention or therapy schedule, which are programmed into data collection unit 111. A combination of strategies 1, 2, and 3 is also possible. (5) Change socks based on one or more properties of the residual limb, such as temperature, moisture level, blood flow, etc., where such properties may be measured by any suitable sensor, such as sensor 115.

The sock management strategy may be incorporated into the clinical interface system for each patient via a program within data collection unit 111 and/or mobile computing device 120. To effect the strategy, the data collection unit 111 and/or mobile computing device 120 may communicate times for sock change and the number and ply of socks to be worn via, e.g., text message, a vibratory alarm, an auditory alarm, and/or another visual alarm such as an LED readout. Each time a sock change is to be done, the data collection unit 111 and/or mobile computing device 120 communicates the change to the patient. If a patient fails to make the sock change within a certain time period (e.g., 5 minutes) then the data collection unit 111 and/or mobile computing device 120 may cue the patient again. In some embodiments, a maximum number of attempts (e.g., three) may be made to communicate the need for sock ply change to the patient. The data collection unit 111 and/or mobile computing device 120 may record the times that alerts are sent and if the sock changes are performed. These data subsequently help inform the practitioner on compliance with the strategy.

Further, in some embodiments, from collected data a practitioner should be able to determine a number of meaningful pieces of information. For example, the practitioner should be able to answer the following questions.

Is a new socket needed?: Thick sock ply additions each day, and frequent additions over the course of the day suggest the need for a new socket. Through extensive clinical use of this monitor and the formation of a clinical database, formal quantitative criteria for socket replacement may be established. At the outset, practitioners use the information with their experience and knowledge of the patient to make their best clinical judgment about socket replacement. Practitioners will also be able to medically justify a new socket to the prescribing physician, health insurance provider, and the patient using this evidence based proof.

Is a new liner needed? Has the patient exceeded the time duration of stand and walk for the liner?: Through extensive data collection and interpretation, new replacement criteria may be created. The new criteria will be use-based standards rather than time based standards.

Is patient education needed on when to change sock ply? Is the patient following practitioner recommendations?: The results might show that the patient is not following practitioner recommendations on how much and when to add sock ply. This result would suggest that patient education efforts need to be pursued to enhance patient compliance. After patient education, the patient can be monitored again to see if compliance is improved. The device informs on the validity of self-reporting for individual patients. If there is little correlation between the patient's self-report and the data then the practitioner might be queried to verify other information provided by the patient relevant to clinical care.

What volume fluctuations is the patient undergoing? What activities are they doing?: If the patient has good sensation the sock changes should reflect volume changes over the course of the day. Greater volume changes typically occur after activity. Thus sock changes should reflect activity. The practitioner is thus informed on the patient's activity patterns.

Is a different intervention needed? For example, is an automated socket volume accommodation strategy needed?: Patients who add socks frequently over the course of the day and then experience limb enlargement overnight might need an automated socket volume accommodation device (suction socket; elevated vacuum; fluid-filled or inflatable inserts; or other technology) to accommodate their volume changes. This instrument not only provides insight into if such a socket design is needed, but also helps to determine if the volume accommodation strategy is effective after it has been added. This instrument may also inform on a prescription of the automated device, for example how large or small a variable volume socket should be allowed, or how strong a vacuum pressure should be set.

Does the patient have an unusual pattern of sock ply change on certain days of the week? If this pattern occurs then the practitioner will query the patient: "What are you doing on those days?" Thus information collected with the sock monitor helps the practitioner gain better insight into his or her patient, information useful to diagnosis and prescription. The new information might help a practitioner diagnose why a patient has an emerging sore on the residual limb, or some other aspects of their health and wellbeing.

In addition to the above examples of using the instrument to collect information to establish a database that facilitates understanding and then subsequent interpretation of the data on new patients, there are other applications. For example, if a link between the days of dialysis treatment and sock ply change are identified, the practitioner can program into the unit a different sock ply change strategy. The unit may help establish rules for Medicare and other programs on when socket replacement is needed. By linking the sock changing activity with the health of the patient, we can set new best practices for prescription for patients.

Potential to assist clinical facilities: The device may assist CPO clinics in inventory and ordering of socks and liners. It is very expensive to keep liners and socks in inventory. If the patient can come in and scan their socks for reorder, much time, energy, and returns could be avoided. Ordering the wrong sock/liner happens all the time, and this problem could be reduced. The instrument may also inform on what type, size, and thickness of socks the patient wears most often and thus which socks and how many socks need to be ordered.

Industry enhancement of products: The instrument will be beneficial for determining if some brands of socks or liners are more durable than others. These quantitative data will set new standards for product life in the industry.

Patient feedback: The system also serves as a feedback device to the patient. For example, the unit may tell a patient if he/she is adhering to the prescribed sock change schedule.

Data to support insurance claims: The system may provide useful information for settlements to insurance companies. Lots of times lawyers ask for a letter pertaining to what the patient will need during a year or a lifetime. These data can help provide that quantitative information and improve the effective use of health care funds.

Clinical interface system 100 in certain embodiments is a distributed computing environment utilizing several computing devices and components that are interconnected via communication links, using one or more computer networks or direct connections. However, it will be appreciated by those of ordinary skill in the art that such a system could operate equally well in a system having fewer or a greater number of components than are illustrated in FIG. 1. Thus, the depiction of clinical interface system 100 in FIG. 1 should be taken as being illustrative in nature, and not limiting to the scope of the disclosure.

Figure 2:
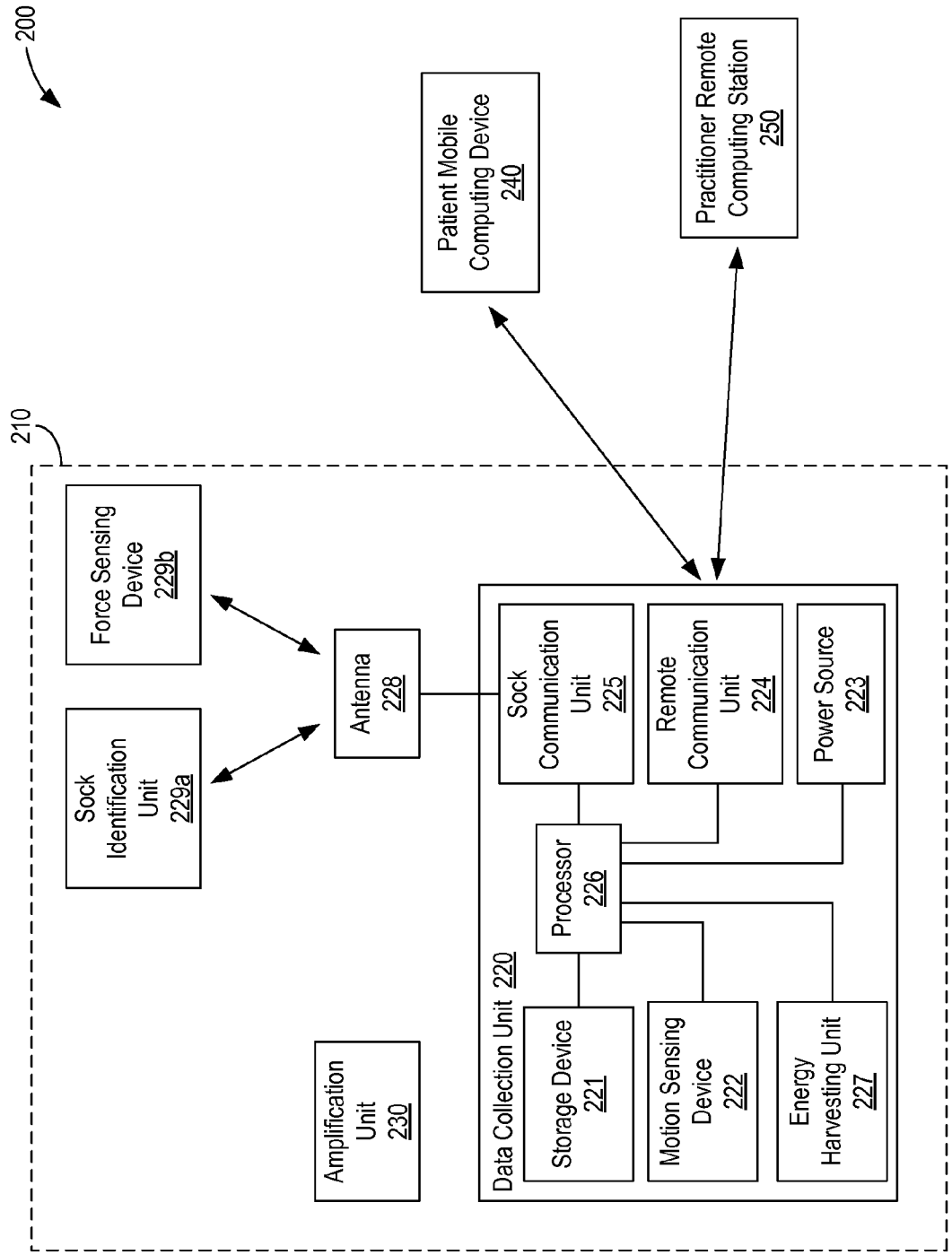
FIG. 2 is a block diagram of a clinical interface system according to an embodiment of the present invention.

FIG. 2 is a block diagram of a clinical interface system 200 according to an embodiment of the present invention. Clinical interface system 200 includes a prosthetic sock monitoring system 210 (which may be similar to sock monitoring system 110) associated with a patient, a mobile computing device 240 (which may be similar to mobile computing device 120) associated with the patient, and a remote computing station 250 (which may be similar to remote computing station 130) associated with a practitioner. In some embodiments, one or more of elements of clinical interface system 200 may be interconnected via a network (not shown) similar to network 140.

Data collection unit 220 includes a number of elements that operate to perform some or all of the functionality described herein. In some embodiments, data collection unit 220 includes a storage device 221, a motion sensing device 222, a power source 223, a remote communication unit 224, a sock communication unit 225, all connected to a processor 226 also provided within data collection unit 220.

Storage device 221 may be any tangible and/or non-transitory computer readable storage media that is operable to store information. The information may be, e.g., information received from motion sensing device 222, sock communication unit 225, and/or remote communication unit 224. For example, storage device 221 may be a random access memory (RAM), a read-only memory (ROM), a magnetic medium such as a hard-drive or a floppy disk, and/or an optical medium such as a CD-ROM. In some embodiments, storage device 221 may be removable. For example, storage device 221 may be a memory card or flash card such as a secure digital (SD) card, a CompactFlash card, a memory stick, etc.

Motion sensing device 222 may be any device operable to detect motion of motion sensing device 222. Motion sensing device 222 may be operable to detect motion using one or more a variety of methods, such as mechanical methods, electronic methods, magnitude detection methods, sound detection methods, reflection methods, vibration methods, etc. Accordingly, motion sensing device 222 may include an accelerometer, a gyroscope, an inclinometer, and/or any other device suitable for measuring or detecting motion. Motion sensing device 222 may be operable to detect motion in one or more dimensions, such as a vertical dimension and one or more horizontal dimensions. In one embodiment, motion sensing device 222 includes one or more accelerometers, where each accelerometer is operable to detect motion in a single dimension. For example, motion sensing device 222 may include an accelerometer for detecting vertical motion. Motion sensing device 222 may be provided at any suitable location for detecting movement of a patient's prosthesis. For example, motion sensing device 222 may be mechanically coupled to prosthesis 112. In at least one embodiment, motion sensing device 222 may be configured to detect motion of a patient picking up their prosthesis 112 to put it on.

In some embodiments, where data collection unit 220 is mechanically coupled to prosthesis 112, motion sensing device 222 may be included in data collection unit 220, as shown in FIG. 2, such that movement of data collection unit 220 would correspond to movement of prosthesis 112. However, in other embodiments, such as where data collection unit 220 is not mechanically coupled to prosthesis 112, motion sensing device 222 may be physically separate from data collection unit 220. In such cases, motion sensing device 222 may communicate with elements of data collection unit 220, such as processor 226, via either a wired or wireless connection between motion sensing device 222 and data collection unit 220.

Power source 223 may be any suitable power supply for supplying power to elements of data collection unit 220. For example, power source 223 may be a DC battery (e.g., 1.5V, 5V, 9V, in a range from 1.5V to 9V, less than 1.5V or greater than 9V) provided within data collection unit 220. Power source 223 may be rechargeable or non-rechargeable and, in some embodiments, include suitable elements for coupling to an external power source (not shown) to charge power source 223.

Remote communication unit 224 may be any suitable hardware and/or software for communicating with devices external to data collection unit 220, such as mobile computing device 240 and/or remote computing station 250. For wired connections, remote communication unit 224 may include any suitable connector, such as an RS232 serial connector, a USB connector, a 10-base-T connector, etc. Further, remote communication unit 224 may be operable to communicate to other devices using any suitable wired or wireless communication protocol, such as Bluetooth, ZigBee, IEEE 802.11, TCP/IP, IrDA, GSM, CDMA, IEEE-488 protocol, USB, PCI, etc.

Sock communication unit 225 may be any suitable hardware and/or software for communicating with one or more sensors (e.g., sensor 115) coupled to prosthetic socks (e.g., prosthetic sock 116) of a patient. For example, sock communication unit 225 may be a radio transceiver coupled to antenna 228 for receiving information communicated from one or more sensors, such as sock identification unit 229a and/or force sensing device 229b.

Sock communication unit 225 may be operable to receive information received via antenna 228 on any one or more of a number of radio frequency bands, such as the very low frequency (VLF) band (3-30 kHz), the low frequency (LF) band (30-300 kHz), the medium frequency (MF) band (300-3000 kHz), the high frequency (HF) band (3-30 MHz), the very high frequency (VHF) band (30-300 MHz), the ultrahigh frequency (UHF) band (300-3000 MHz), the super high frequency (SHF) band (3-30 GHz), the extremely high frequency (EHF) band (30-300 GHz), and the tremendously high frequency (THF) band (300-3000 GHz). In one particular embodiment, sock communication unit 225 may be operable to receive information at 433 MHz. However, sock communication unit 225 is not limited to these bands, nor is it limited to radio frequency bands. For example, sock communication unit 225 may be operable to receive information communicated over other parts of the electromagnetic spectrum, such as microwaves, infrared radiation, etc.

In some embodiments, sock communication unit 225 may be operable to receive information from one or more sensors only when such sensors are within a detection range. The detection range may depend on a variety of elements, such as the sensitivity of signal processing units of sock communication unit 225, the sensitivity of antenna 228, the output power of antenna 228 and/or the sensors, and orientation of antenna 228 to one or more antennas of the sensors. In some embodiments, the detection range may be approximately 0.5 m, 1 m, 1.5 m, 2 m, in a range from 0.5 m to 2 m, less than 0.5 m, or greater than 2 m.

Sock communication unit 225 may be operable to acquire a variety of information from one or more sensors, such as sock identifiers, sock characteristics, force information, displacement information, etc. Sock communication may be operable to acquire a variety of other information as well, such as a tag identifier (in the case of using RFID tags), a source of transmission, a source antenna, the type of source (e.g., the type of RFID tag), and the length of the source transmission (e.g., the length of the RFID tag). In some embodiments, such information may be synchronized with a time provided by any suitable time source (e.g., a clock provided in data collection unit 220). Accordingly, a timestamp may be associated with each piece of information received from each sensor within range of antenna 228.

In some embodiments, sock communication unit 225 may poll for sensors only after certain intervals of time or in response to some stimulus (e.g., motion detected by motion sensing device 222). For example, sock communication unit 225 may poll for sensors at a rate of 1 sample per 15 seconds, 1 sample per 30 seconds, 1 sample per minute, 1 sample per 2 minutes, 1 sample per 5 minutes, or in a range from 1 sample per 15 seconds to 1 sample per 5 minutes, or at a rate faster than 1 sample per 15 seconds or slower than 1 sample per 5 minutes. In some embodiments, the sampling rate may depend on the intended use of the received data. For example, for gait characterizations, a rate of 1 to 20 Hz may be used, and to identify high frequency events from a jump or fall, for example, an even faster sampling rate may be used, such as up to 175 Hz. Accordingly, sampling rates may also be in a range from 1 Hz to 250 Hz, or greater than 250 Hz.

Energy harvesting unit 227 may be any device operable to generate energy. Energy harvesting unit 227 may be operable to generate energy from one or more of a number of different sources, such as movement of the patient (and/or data collection unit 220 and/or energy harvesting unit 227), impact of the patient or prosthesis with a supporting surface, heating of the patient (and/or data collection unit 220 and/or energy harvesting unit 227), perspiration of the patient (and/or data collection unit 220 and/or energy harvesting unit 227), etc. For example, energy harvesting unit 227 may include piezoelectric material for converting mechanical stress (such as that applied by a patient's weight or movement) into electricity, a thermocouple for converting temperature gradients (such as the difference between a patient's body temperature and an outside temperature) into electricity, a solar cell for converting light into electricity, etc.

In some embodiments and as shown in FIG. 2, energy harvesting unit 227 may be part of data collection unit 220 and coupled to, e.g., power source 223 or other elements of data collection unit 220 so as to provide energy to elements of data collection unit 220. In other embodiments, energy harvesting unit 227 may be separate from data collection unit 220, but coupled to data collection unit 220 so as to transfer generated energy to elements of data collection unit 220. Further, in at least one embodiment, energy harvesting unit 227 may be part of one or more elements of prosthetic sock monitoring system 210, such as sock identification unit 229a and/or force sensing device 229b, so as to provide energy to those respective devices.

Antenna 228 may be any suitable device for receiving wireless transmissions from one or more sensors such as sock identification unit 229a and/or force sensing device 229b. Accordingly, antenna 228 may be operable to receive wireless transmissions over any of the aforementioned bands. Antenna 228 may have any suitable structure for receiving such wireless transmissions. For example, antenna 228 may be a wire antenna (such as a dipole antenna, monopole antenna, a zig-zag antenna, loop antenna, etc.), a microstrip antenna (e.g., a rectangular microstrip antenna), a reflector antenna (e.g., a parabolic reflector), a travelling wave antenna (e.g., a helical antenna, yagi-uda antenna, spiral antenna, etc.), an aperture antenna (e.g., a slot antenna, an inverted-F antenna, a horn antenna, a slotted waveguide antenna, etc.), or other suitable antenna (e.g., a near field communication antenna).

Sock identification unit 229a may include any suitable hardware and/or software for providing information indicative of one or more characteristics of a prosthetic sock associated with sock identification unit 229a. For example, sock identification unit 229a may be operable to indicate a thickness of the prosthetic sock (e.g., 1-ply, 2-ply, 3-ply, etc.), a shape of the sock (e.g., cylindrical, conical, spherical, etc.), a material of the sock (e.g., cotton, wool, synthetic fiber, etc.), a size of the sock (e.g., small, medium, large), breathability of the prosthetic sock, elasticity of the prosthetic sock, etc. In some embodiments, sock identification unit 229a may be operable to provide an identifier that identifies a particular sock. For example, each of a plurality of socks may have a unique identifier. The unique identifier may then be associated with one or more characteristics of the prosthetic sock. Such an association may be stored by data collection unit 220, such as in a database of storage device 221, or some other device.

In some embodiments, sock identification unit 229a may be self-powered. For example, sock identification unit 229a may include one or more batteries or other power sources for providing information to data collection unit 220. In other embodiments, sock identification unit 229a may not include any batteries or power sources, but rather may acquire power from an external supply. For example, sock identification unit 229a may receive power communicated from data collection unit 220 via, e.g., antenna 228. Further, sock identification unit 229a may include any suitable elements for communicating information to sock identification unit 229a over any suitable frequency band using any suitable communication protocol, and thus may include any suitable antenna or antennas for facilitating such communication. In some embodiments, sock identification unit 229a may be a passive radio frequency (RF) tag and/or an active RF tag. In one particular embodiment, sock identification unit 225 may be operable to communicate information at 433 MHz. Sock identification unit 229a may be flexible such that it does not interfere with the mobility or comfort of a patient's residual limb 117, or may be inflexible as long as it is small enough (e.g., having an area of 1 cm$^2$, 2 cm$^2$, 3 cm$^2$, 4 cm$^2$, 5 cm$^2$, in a range from 1 cm$^2$ to 5 cm$^2$, or less than 1 cm$^2$) such that it does not interfere with the mobility or comfort of the patient's residual limb 117.

Force sensing device 229b may include any suitable hardware and/or software for providing information indicative of an amount of force applied to force sensing device 229b. For example, force sensing device 229b may be a strain gage (e.g., a foil strain gage, a semiconductor strain gage, a thin-film strain gage, a wire strain gage, etc.), a piezoresistive film force sensor, a piezoelectric crystal force transducer, a pressure sensor, or other type of force measuring system (e.g., an elastic device, a magneto-elastic device, etc.). Force sensing device 229b may be operable to indicate an amount of force applied to force sensing device 229b by, e.g., residual limb 117 and/or prosthesis 112. In some embodiments, in addition or alternative to providing an indication as to amount of force, force sensing device 229b may provide an indication that an amount of force greater than a threshold amount has been applied to force sensing device 229b.

In some embodiments, force sensing device 229b may be self-powered. For example, force sensing device 229b may include one or more batteries or other power sources for providing information to data collection unit 220. In other embodiments, force sensing device 229b may not include any batteries or power sources, but rather may acquire power from an external supply. For example, force sensing device 229b may receive power communicated from data collection unit 220 via, e.g., antenna 228. Further, force sensing device 229b may include any suitable elements for communicating information to sock communication unit 225 over any suitable frequency band using any suitable communication protocol, and thus may include any suitable antenna or antennas for facilitating such communication. In one particular embodiment, sock identification unit 225 may be operable to communicate information at 433 MHz. In some embodiments, data collection unit 220 may be a piezoelectric film sensor, a piezoresistive film sensor, a capacitive film sensor, and/or an optical pressure sensor. Force sensing device 229b may be flexible such that it does not interfere with the mobility or comfort of a patient's residual limb 117, or may be inflexible as long as it is small enough (e.g., having an area of 1 cm$^2$, 2 cm$^2$, 3 cm$^2$, 4 cm$^2$, 5 cm$^2$, in a range from 1 cm$^2$ to 5 cm$^2$, or less than 1 cm$^2$) such that it does not interfere with the mobility or comfort of the patient's residual limb 117.

It should be recognized that in some embodiments, force sensing device 229b may not be provided as part of prosthetic sock 116 but may be coupled to prosthesis 112. For example, force sensing device 229b may be arranged within socket 113. Force sensing device 229b may then, in some embodiments, be wired to processor 226 and/or sock communication 225.

In addition to, alternatively to, or integrated with, sock identification unit 229a and/or force sensing device 229b, the sensors may include one or more energy harvesting devices. That is, an energy harvesting device may be coupled to prosthetic sock 116 to aid the sensors in communicating information to data collection unit 111. The energy harvesting device may harvest one or more different types of energy, such as forces applied to prosthetic sock, acceleration/deceleration of prosthetic sock, temperature of prosthetic sock, humidity of prosthetic sock, etc. The energy harvesting device may be coupled to the one or more sensors or, in some embodiments, may be part of the one or more sensors. For example, in one embodiment, force sensing device 229b may be operable to measure force and harvest energy. A number of different devices may be used to facilitate such functionality, such as a piezoelectric element. Further, in some embodiments, a piezoelectric element may also be operable to assist data collection unit 111 or other devices in identifying when a sock is near prosthesis 112 but not worn.

Amplification unit 230 is a device operable to amplify one or more signals. In one embodiment, amplification unit 230 may operate to amplify signals received from sock identification unit 229a, whereas in another embodiment, amplification unit 230 may operate to amplify signals received from force sensing device 229b. Amplification unit 230 may be provided at one or more suitable locations in clinical interface system 200 to amplify signals. For example, amplification unit 230 may be provided between antenna 228 and processor 226, such as in sock communication unit 225, so as to amplify signals received by antenna 228 and provide the amplified signals to processor 226. Accordingly, in at least one embodiment, amplification unit 230 may be coupled to one or more of antenna 228, sock communication unit 225, and processor 226. Examples of amplification unit 230 are further discussed with reference to FIGS. 4A and 4B.

Patient mobile computing device 240 and practitioner remote computing station 250 may operate similar to and include similar components as mobile computing device 120 and remote computing station 130, respectively, previously described with reference to FIG. 1. Accordingly, further description is omitted.

In accordance with one embodiment, upon activating data collection unit 220, processor 226 may repeatedly execute a collect and store sequence. Periodically, e.g., seven times within each one-second period, processor 226 may send a command to sock communication unit 225 (e.g., an RFID transceiver) requesting an inventory of sock identification units (e.g., RFID tags) in the range of antenna 228. Sock identification units that are within range of antenna 228 may then respond with information such as a unique identifier identifying the prosthetic sock coupled to sock identification unit 229a. Inventory (any tag recognized during the seven sequences is recorded once), and the list is stored to processor 226. In some embodiments, before processor 226 sends another inventory command, it saves the tag inventory byte stream to a text file or other data structure on storage device 221. Using this technique, data on storage device 221 is constantly updated thus ensuring no data is lost if the system is turned off. The system may operate continuously, for a number of hours, days, months, etc.

Figure 11A:
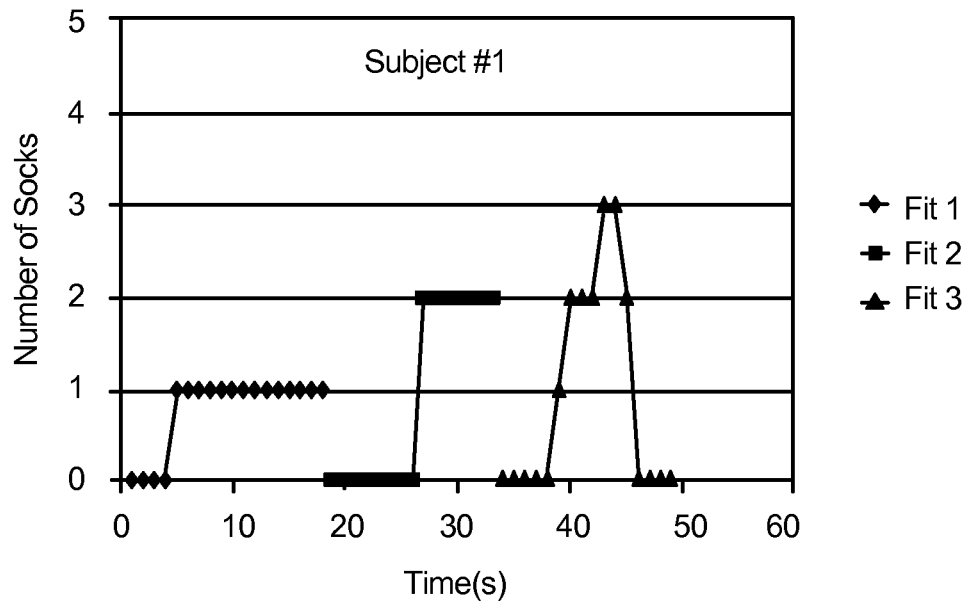
FIG. 11A shows a number of socks worn by a patient over a time period.

Turning briefly to FIG. 11A, FIG. 11A shows a number of socks worn by a patient over a time period. According to some embodiments, sock communication unit 225 may simultaneously receive unique identifiers indicating the presence or absence of one or more prosthetic socks. Accordingly, processor 226 may be operable to store such information in storage device 221 and/or process such received information to generate analysis data or, in some embodiments, communicate such information to a remote computing device such as mobile computing device 240 and/or remote computing station 250 for processing. Such devices may be operable to process such data to determine the number of prosthetic socks worn by a patient over a period of time. For example, as shown in FIG. 11A, such devices may determine that for approximately 20 seconds, the patient wore one prosthetic sock ("Fit 1"), then for a subsequent 35 seconds, the patient wore two prosthetic socks ("Fit 2"), and then for a subsequent 15 seconds, the patient wore three prosthetic socks ("Fit 3").

In some embodiments, data collection unit 220 may independently or simultaneously receive information from multiple sensors such as sock identification unit 229a and force sensing device 229b, regardless of whether the sensors are the same (e.g., multiple sock identification unit 229 on one or multiple socks) or different (e.g., both a sock identification unit 229a and a force sensing device 229b disposed on one sock). Force information received by force sensing device 229b may be processed to determine one or more activities of the patient. For example, an amount of force, frequency of force, or other characteristics of the received force information may be processed by, e.g., processor 226, mobile computing device 240, and/or remote computing station 250, to determine an activity, or inactivity, of the patient. The activity may be, for example, standing, or may be a dynamic activity, such as walking, running, climbing stairs, lateral shifting, donning of a prosthetic sock, doffing of a prosthetic sock, etc. Further, in at least one embodiment, any one or more of processor 226, mobile computing device 240, and/or remote computing station 250 may correlate determined activities of the patient with determinations indicating the number of socks worn by the patient.

Figure 11B:
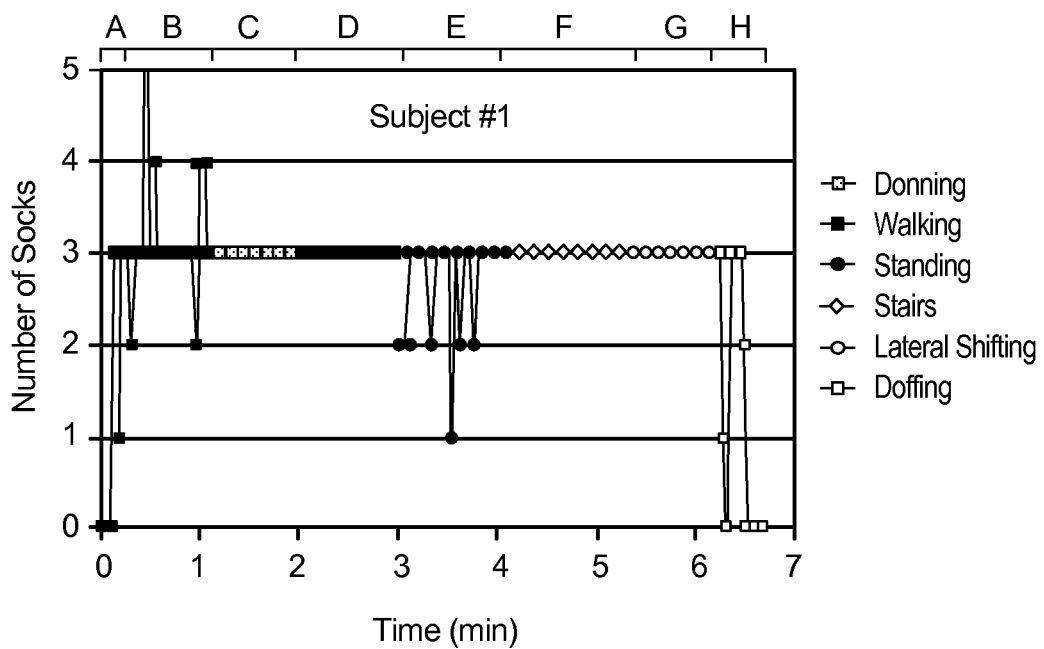
FIG. 11B shows a number of socks worn by a patient over a time period correlated with an activity of the patient.

Turning briefly to FIG. 11B, FIG. 11B shows a number of socks worn by a patient over a time period correlated with an activity of the patient. In this embodiment, the time period ranges from 0 to 7 minutes, and correlates a number of socks with activities including donning a prosthetic sock, walking, standing, walking up and/or down stairs, lateral shifting, and doffing a prosthetic sock. For example, while donning socks, a number of socks identified changes from 0 to 3 during a first portion (A) of the time period. While walking, the number of socks identified varies from 2 socks to 5 socks during a second portion (B) of the time period. The variation from 3 socks was error. While standing, the number of socks identified was 3 during a third portion (C) of the time period. While walking again, the number of socks identified was 3 during a fourth portion (D) of the time period. While walking up and down stairs, the number of socks identified varied from 1 to 3 socks during a fifth period (E) of the time period, where the variation from 3 socks was error. While walking again and lateral shifting, during sixth (F) and seventh (G) portions of the time period, the number of socks identified was 3, and while doffing the socks during an eighth portion (H) of the time period, the number of socks identified varied from 3 to 0.

In some embodiments, performance of prosthetic sock monitoring system 210 may be validated to ensure results are insensitive to sources of error likely to be encountered during clinical use, including limb-socket pistoning, use of carbon fiber sockets, repetitive mechanical loading, and/or sock presence local to the prosthesis but not worn by the user. To validate the activity detection capabilities of the sensors (e.g., force sensing device 229b), data is collected by data collection unit 220 simultaneously with an activity monitor (e.g., StepWatch™, Orthocare™, etc.) shown to be very reliable (e.g., 98% or greater) in related prosthetic applications. Because the data collection unit 220 may record pressure or force, it may measure both standing and activity durations, as opposed to just step counts. However, a computing device (e.g., processor 226, mobile computing device 240, and/or remote computing station 250) may determine step counts based on the pressure/force and time information received from force sensing device 229b.

Sock monitoring system 210 may employ one or more power saving techniques in addition or alternatively to those already described herein. In one embodiment, where sensors include one or more RFID tags and sock communication unit 225 comprises an RFID reader, offset transmissions may be used instead of RF backscatter. For example, a battery-free RFID tag may receive power and/or data at a frequency $f_1$ (e.g., the RFID reader may communicate data at 915 MHz) The RFID tag then internally generates a different frequency ($f_{1/2}$ or $f_{1/3}$) and radiates RF power and/or data back to the reader at the different frequency (e.g., at a frequency of 305 MHz). This greatly simplifies the architecture of the RFID reader, thereby advantageously reducing complexity and power requirements of the sock communication unit 225.

In another embodiment, data collection unit 220 may sample the sensors based on an activity of the user. For example, upon determining that the patient is standing or walking, sock communication unit 225 may poll for sensors (e.g., force sensing device) at a first rate, such as 20 samples per second. Upon determining that the patient is sitting, sock communication unit 225 may poll for sensors at a second rate, such as 1 sample per 15 seconds. Upon determining that the prosthesis is not being worn, sock communication unit 225 may not poll for sensors for at least certain period of time after removal, such as 30 seconds, and after that at a third rate, such as 1 sample per 30 seconds.

In some embodiments, a force sensor provided within the socket 103 may be used to power data collection unit 111 and, in some embodiments, determine the sampling rate as discussed above. The force sensor may identify when the socket is doffed and, communicating the signal to processor 226, processor 226 may in response cause the power to be turned off when the prosthesis is not worn. Similarly, when a force is sensed by the force sensor, the force sensor may communicate the signal to processor 226, and processor 226 may in response cause the power to be turned back on when the prosthesis is worn.

Clinical interface system 200 in certain embodiments is a distributed computing environment utilizing several computing devices and components that are interconnected via communication links, using one or more computer networks or direct connections. However, it will be appreciated by those of ordinary skill in the art that such a system could operate equally well in a system having fewer or a greater number of components than are illustrated in FIG. 2. Thus, the depiction of clinical interface system 200 in FIG. 2 should be taken as being illustrative in nature, and not limiting to the scope of the disclosure. For example, data collection unit 220 may include a display for displaying information to the user, such as information instructing the user when to don a sock, what type of sock the user should don, and, in some embodiments, the number of socks detected by the data collection unit 220.

FIG. 3 is a diagram of a computer apparatus 300, according to an example embodiment. Numerous computing devices described herein, such as mobile computing device 120 and/or remote computing station 130, may use any suitable number of subsystems in the computer apparatus to facilitate the functions described herein. Examples of such subsystems or components are shown in FIG. 3. The subsystems shown in FIG. 3 are interconnected via a system bus 310. Additional subsystems such as a printer 320, keyboard 330, fixed disk 340 (or other memory comprising tangible and/or non-transitory computer-readable media), monitor 350, which is coupled to display adapter 355, and others are shown. Peripherals and input/output (I/O) devices (not shown), which couple to I/O controller 360, can be connected to the computer system by any number of means known in the art, such as serial port 365. For example, serial port 365 or external interface 370 can be used to connect the computer apparatus to a wide area network such as the Internet, a mouse input device, or a scanner. The interconnection via system bus allows the central processor 380 to communicate with each subsystem and to control the execution of instructions from system memory 390 or the fixed disk 340, as well as the exchange of information between subsystems. The system memory 390 and/or the fixed disk 340 may embody a tangible, non-transitory computer-readable medium.

Computer apparatus 300 in certain embodiments is a system of computing elements that may be implemented with one or more of the computing devices described herein. However, it will be appreciated by those of ordinary skill in the art that such an apparatus could operate equally well with fewer or a greater number of components than are illustrated in FIG. 3. Thus, the depiction of computer apparatus 300 in FIG. 3 should be taken as being illustrative in nature, and not limiting to the scope of the disclosure.

Figure 4A:
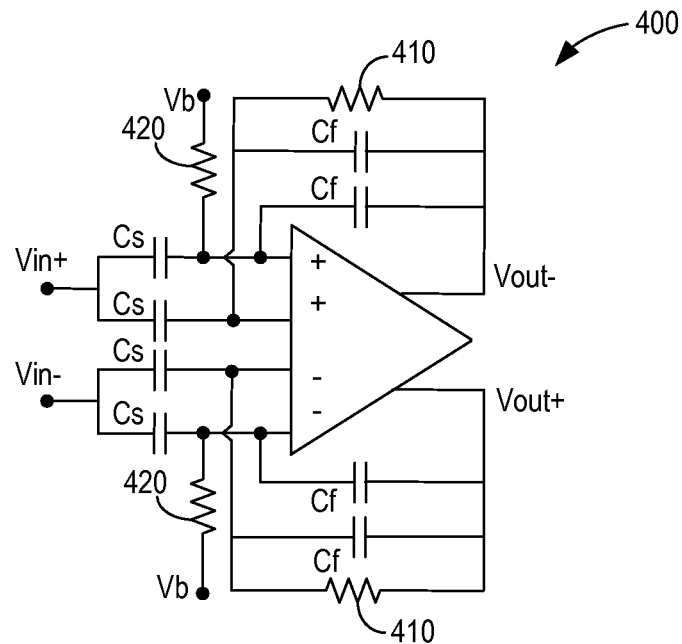
FIG. 4A is a circuit diagram of an amplifier according to an embodiment.
Figure 4B:
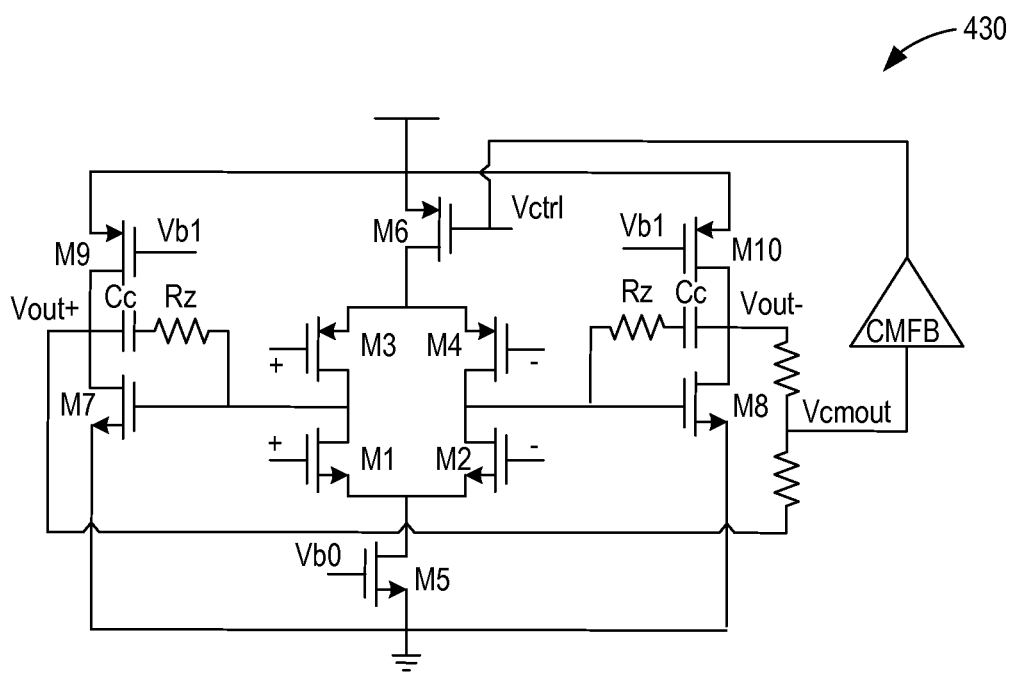
FIG. 4B is a circuit diagram of a differential amplification unit according to an embodiment.

FIGS. 4A and 4B are circuit diagrams of an amplifier 400 according to an embodiment. In some embodiments, amplifier 400 may be implemented in, e.g., data collection unit 220, to increase the sensitivity of data collection 220 to receiving signals from sensors such as sock identification unit 229a while reducing the amount of power consumption from, e.g., power source 223. For example, amplifier 400 may be implemented as the amplification unit 230 discussed with reference to FIG. 2. However, in other embodiments, amplifier 400 may be implemented in other computing devices, integrated circuits, etc., to increase the signal to noise level of a given input voltage while reducing power consumption.

FIGS. 4A and 4B generally show an amplifier design that achieves low noise performance with minimal power consumption under low supply voltages. A telescopic-cascode closed-loop amplifier ensures power-supply rejection (PSR), common-mode rejection (CMR) and linearity performance. An open-loop complementary-input amplifier gives better noise performance for a given power budget, at the expense of reduced linearity performance and reduced PSR. Leveraging the same power-efficient complementary-input topology, the amplifier improves the linearity and PSR performance by utilizing a fully-differential, closed-loop architecture. Consistent with theory, the telescopic amplifier has comparable noise-efficiency factor (NEF) compared to the prior state-of-the-art while ensuring operation under low power supplies. The open-loop amp and the closed-loop complementary amp have significantly better power-noise performance than the telescopic due to the power-efficient complementary-input topology. The three low noise amplifiers exhibit low noise performance of 3.1 µV, 3.5 µV and 2 µV while consuming ultra-low power of 12 µW, 0.8 µW, and 12 µW, respectively. The amplifiers can be effectively used in multi-channel biopotential recording applications as described herein, where power consumption of the low-noise front-end is to be minimized, or in other applications where it is desired to increase signal to noise ratio with minimal power consumption. These amplifiers may advantageously be made extremely small.

FIG. 4A shows an amplification circuit 400 according to an embodiment. Amplification circuit 400 includes a number of capacitors (Cf) coupled in parallel with each other and in parallel with resistors 410, and which are wired across input and output elements of a differential amplification unit 430. Input capacitors (Cs) and resistors 420 are wired to the inputs of differential amplification unit 430, where input voltages are applied to the input capacitors (Cs) and output voltages are read from the outputs of differential amplification unit 430.

FIG. 4B shows details for a differential amplification unit 430 according to an embodiment. Differential amplification unit 430 includes a number of transistors (M1 to M4) having sources and drains coupled to one another and gates that receive the voltages input to differential amplification unit 430. One of the differential output voltages (Vout+) is drawn from additional transistors (M7 and M9) coupled to a capacitor (Cc) and resistor (Rz) connected between a first pair of input transistors (M1 and M3). The other of the differential output voltages (Vout−) is drawn from additional transistors (M8 and M10) coupled to a capacitor (Cc) and resistor (Rz) connected between a second pair of input transistors (M2 and M4).

Amplifier 400 in certain embodiments is an amplification circuit including a differential amplifier having a number of interconnected transistors, capacitors, and resistors. However, it will be appreciated by those of ordinary skill in the art that such an amplification unit is not necessary, but rather other types of devices for increasing signal to noise ratio may be used. Thus, the depiction of amplifier 400 in FIGS. 4A and 4B should be taken as being illustrative in nature, and not limiting to the scope of the disclosure.

Figure 5A:
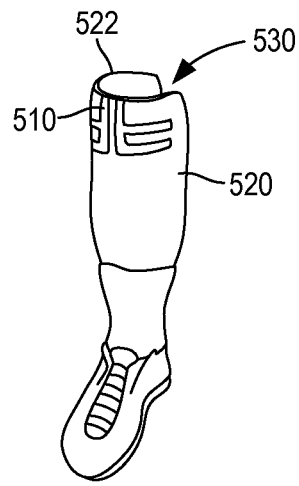
FIG. 5A shows an antenna coupled to a prosthesis according to a first embodiment.

FIG. 5A shows an antenna 510 coupled to a prosthesis 520 according to a first embodiment. Antenna 510 may be operable to receive signals from one or more sensors, such as sensor 115, and may be coupled to a computing device such as data collection unit 111 to communicate received signals to that computing device.

Antenna 510 according to this embodiment is bonded to an exterior surface of a socket 530 of prosthesis 520, and extends from a brim 522 of prosthesis 520 toward an end opposite the end at which the brim is located. Antenna 510 may be made of any one or more conductive materials for generating current in response to being exposed to an electromagnetic wave, magnetic wave, microwave, or other type of radiation, including one or more metals (e.g., copper, silver, gold, etc.) and/or non-metals (e.g., a conductive polymer, graphite, plasma, etc.). Antenna 510 may extend partially or entirely along a length of socket 530, and may wrap around either a portion or an entire circumference of socket 530.

In accordance with some embodiments, an insulative layer (not shown) may be disposed between antenna 510 and the surface of prosthesis 520. The insulative layer may be made from insulating material operable to electrically and/or thermally insulate antenna 510 from prosthesis 520. For example, the insulative layer may include one or more of glass, porcelain, composite polymer materials, silicon, rubber, polyethylene, rubber-like polymers, oil impregnated paper, polyvinyl chloride, etc. In some embodiments, the insulative material may also operate to bond antenna 510 to prosthesis 520, while in other embodiments antenna 510 may be bonded via a separate bonding layer (e.g., glue or other adhesive) arranged between the insulative material and prosthesis 520 or via a separate bonding element (e.g., one or more scripts, nails, clamps, etc.). Further, in some embodiments, the insulative layer may have the same shape as antenna 510 (and, in at least one embodiment, a shape that is slightly larger than that of antenna 510), while in other embodiments, the insulative layer may be applied only between select portions of antenna 510 and prosthesis 520. Whether an insulative layer is provided may, in some embodiments, depend on the type of prosthesis 520. For example, when the prosthesis 520 is made of conductive materials, an insulative layer may be provided, whereas when the prosthesis is made of non-conductive materials, the insulative layer may be omitted.

Figure 5B:
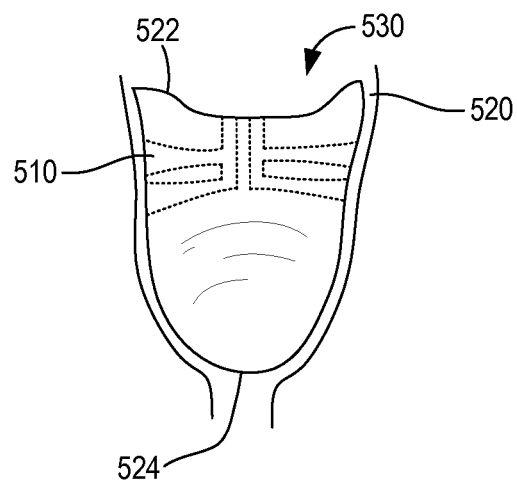
FIG. 5B is a cross-sectional diagram of the prosthesis of FIG. 5A.

FIG. 5B is a cross-sectional diagram of the prosthesis of FIG. 5A. From the cross-sectional diagram, it is apparent that antenna 510 may extend only partially from brim 522 toward an end 524 of socket 530 arranged opposite brim 522. In other embodiments, antenna 510 may extend all the way to end 524 of socket 530.

Figure 6A:
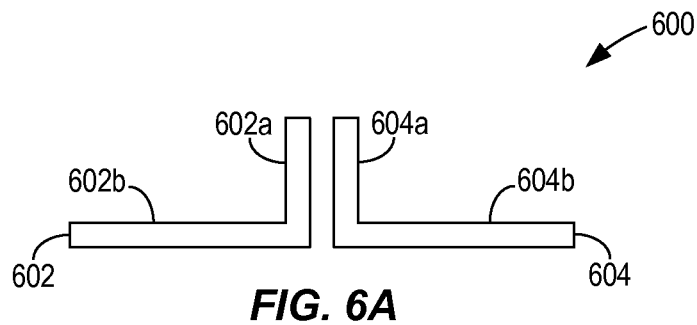
FIG. 6A shows an antenna according to a first embodiment.

FIG. 6A shows an antenna 600 according to a first embodiment. Antenna 600 is a dipole antenna that may be used in or on a prosthesis such as prosthesis 112 to receive signals from one or more sensors, such as sensor 115. In some embodiments, antenna 600 may be coupled to a computing device such as data collection unit 111 to communicate received signals to or from that computing device. Antenna 600 includes a first element 602 and a second element 604, where first element 602 includes a first portion 602a coupled to a second portion 602b, and second element 604 includes a first portion 604a coupled to a second portion 604b. First portion 602a is in parallel with first portion 604a, and first portion 602a and first portion 604a may be coupled to a device for receiving signals propagated to antenna 600, such as data collection unit 111, via any suitable coupling mechanism, such as a coaxial cable. Further, second portion 602b extends in a direction away from second portion 604b. In at least one embodiment, a length of antenna 600 may be determined based on one or more of a desired frequency for communicating with data collection unit 220, the composition of prosthesis 112, and/or the size of prosthesis 112.

Figure 6B:
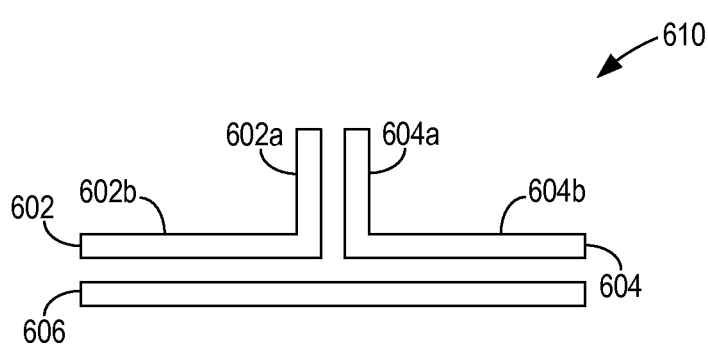
FIG. 6B shows an antenna according to a second embodiment.

FIG. 6B shows an antenna 610 according to a second embodiment. Antenna 610 is similar to that discussed with reference to FIG. 6A, except in this embodiment antenna 610 includes a third element 606 arranged in parallel with second portion 602b and second portion 604b. In the embodiment shown in FIG. 6B, third element 606 has a length the same as the combined length of second portion 602b and second portion 604b when arranged with a space between second portion 602b and second portion 604b, but in other embodiments may be shorter or longer than that combined length.

Figure 6C:
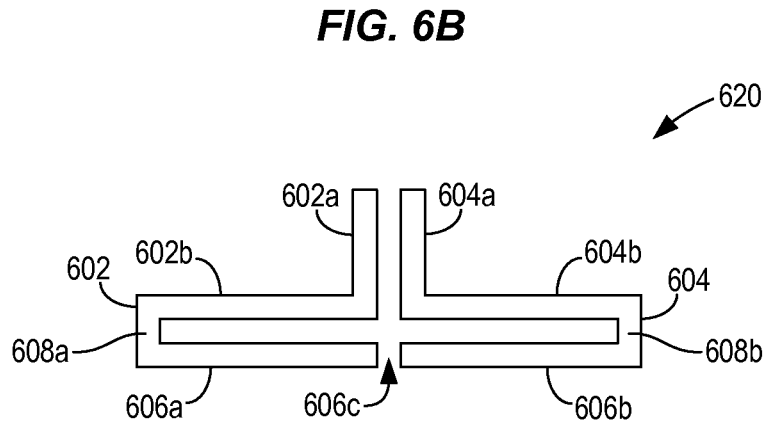
FIG. 6C shows an antenna according to a third embodiment.

FIG. 6C shows an antenna 620 according to a third embodiment. Antenna 620 is similar to that discussed with reference to FIG. 6B, except in this embodiment third element 606 is separated into a first portion 606a and a second portion 606b. In this embodiment, first portion 606a and second portion 606b are separated by a gap 606c equal to a size of a gap between second portion 602b and second portion 604b. However, in other embodiments, first portion 606a and second portion 606b may be separated by a gap larger than or smaller than the size of the gap between second portion 602b and second portion 604b. Further, first portion 606a is electrically coupled to second portion 602b via a first connecting element 608a provided at an end of first portion 606a opposite gap 606c, and second portion 606b is electrically coupled to second portion 604b via a second connecting element 608b provided at an end of second portion 606b opposite gap 606c, where first connecting element 608a and second connecting element 608b are in parallel with one another and with first portion 602a and second portion 604a.

Figure 6D:
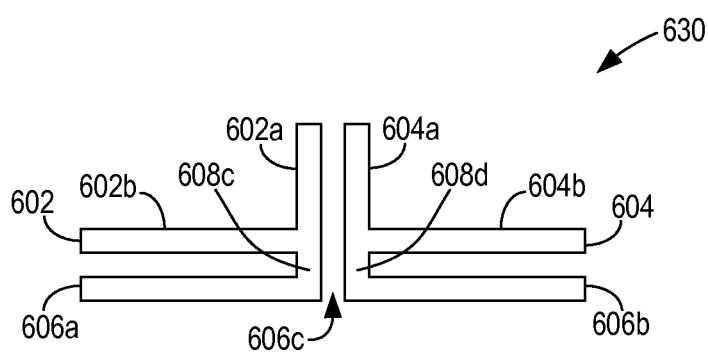
FIG. 6D shows an antenna according to a fourth embodiment.

FIG. 6D shows an antenna 630 according to a fourth embodiment. Antenna 630 is similar to that discussed with reference to FIG. 6C, except in this embodiment first portion 606a and second portion 606b are respectively coupled to, and extend in the same direction as, first portion 602a and second portion 602b, via a third connecting element 608c and a fourth connecting element 608d located at the end of first portion 606a and second portion 606b proximate gap 606c rather than opposite gap 606c. In at least one embodiment, gap 606c may at least in part be used to control the resonant frequency and thus tune the antenna to the individual patient's socket. Accordingly, gap 606c may be determined based on the desired communication frequency. This and other features of the disclosed antenna designs may advantageously increase the gain for certain signals received in certain frequency bands, such as the UHF band.

Figure 7:
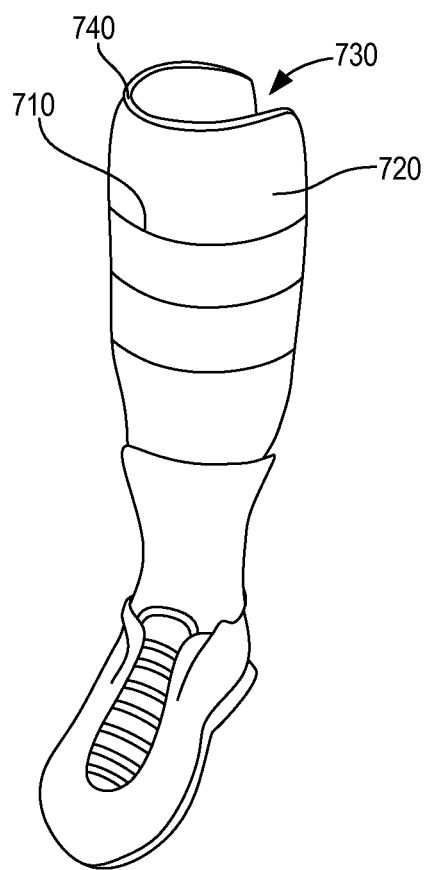
FIG. 7 shows an antenna coupled to a prosthesis according to a second embodiment.

FIG. 7 shows an antenna 710 coupled to a prosthesis 720 according to a second embodiment. In this embodiment, antenna 710 is a helical antenna that includes a conductive wire wound around prosthesis 720. The conductive wire may be bonded to and, in some embodiments insulated from, prosthesis 720 using an insulative and/or bonding layer similar to that discussed with reference to FIGS. 5A and 5B. The wire may be of any suitable gauge, may wrap around prosthesis 720 any suitable number of times, and have any suitable pitch between wrappings, for receiving information from one or more sensors in a particular frequency band. Further, while in this embodiment the helical antenna is mechanically coupled to an exterior surface of prosthesis 720, in other embodiments the helical antenna may be mechanically coupled to an interior surface of prosthesis 720. For example, the helical antenna may be mechanically coupled to a surface of socket 730. In yet another embodiment, instead of wrapping around prosthesis 720, the helical antenna may be a wire wrapped around the brim 740 of prosthesis 720. In at least one embodiment, a length of antenna 710 may be determined based on one or more of a desired frequency for communicating with data collection unit 220, the composition of prosthesis 112, and/or the size of prosthesis 112.

Figure 8A:
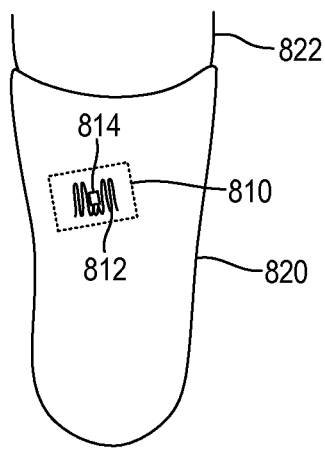
FIG. 8A shows a sensor coupled to a prosthetic sock according to a first embodiment.

FIG. 8A shows a sensor 810 coupled to a prosthetic sock 820 according to a first embodiment. Sensor 810 in accordance with this embodiment is an RFID tag having a "square" inlay. For example, the antenna 812 and circuitry 814 coupled to antenna 812 may form a square shape, where circuitry 814 is operable to store and communicate identification or other characteristic information concerning prosthetic sock 820. One of ordinary skill in the art would recognize that other types of RFID tags may be used, having any suitable shape and/or size. In at least one embodiment, sensor 810 may be arranged on prosthetic sock 820 such that, when prosthetic sock 820 is disposed over the patient's residual limb 822 and inserted into the socket of the prosthesis, the antenna 812 is arranged in a center of an antenna (e.g., antenna 510) located in the socket of the prosthesis. Further, in at least one embodiment, sensor 810 may be arranged on prosthetic sock 820 such that, when prosthetic sock 820 is disposed over the patient's residual limb 822 and inserted into the socket of the prosthesis, the face of antenna 812 is arranged in parallel with the face of an antenna (e.g., antenna 510) located in the socket of the prosthesis.

Figure 8B:
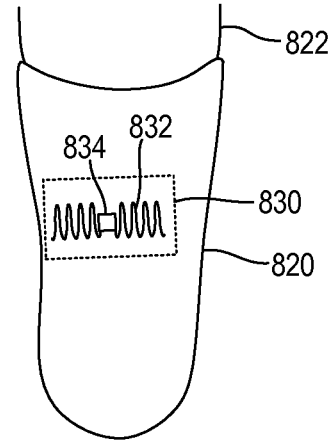
FIG. 8B shows a sensor coupled to a prosthetic sock according to a second embodiment.

FIG. 8B shows a sensor 830 coupled to a prosthetic sock 820 according to a second embodiment. Sensor 830 in accordance with this embodiment is an RFID tag having a "squig" inlay. For example, the antenna 832 and circuitry 834 coupled to antenna 832 may form a rectangular shape, where circuitry 814 is operable to store and communicate identification or other characteristic information concerning prosthetic sock 820. One of ordinary skill in the art would recognize that other types of RFID tags may be used, having any suitable shape and/or size.

Figure 8C:
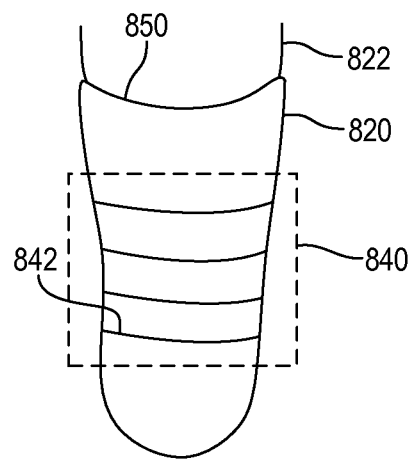
FIG. 8C shows a sensor coupled to a prosthetic sock according to a third embodiment.

FIG. 8C shows a sensor 840 coupled to a prosthetic sock 820 according to a third embodiment. Sensor 840 in accordance with this embodiment is an RFID tag having a helical-shaped antenna 842 coupled to circuitry (not shown), where the circuitry is operable to store and communicate identification or other characteristic information concerning prosthetic sock 820.

In this embodiment, antenna 842 is a helical antenna that includes a conductive wire wound around prosthetic sock 820. The conductive wire may be bonded to prosthetic sock 820 using an insulative and/or bonding layer similar to that discussed with reference to FIGS. 5A and 5B. The wire may be of any suitable gauge, may wrap around prosthetic sock 820 any suitable number of times, and have any suitable pitch between wrappings, for communicating information from the coupled circuitry.

While in this embodiment the helical antenna is mechanically coupled to an exterior surface of prosthetic sock 820, in other embodiments the helical antenna may be mechanically coupled to an interior surface of prosthetic sock 820. In yet other embodiments the conductive wire may be sewn within the material of prosthetic sock 820.

In some embodiments, instead of wrapping around prosthetic sock 820, the helical antenna may be a wire wrapped around the brim 850 of prosthetic sock 820. The use of a helical antenna in the prosthetic sock may be particularly advantageous when a helical antenna is also used in the prosthesis, in that coupling between the two antennas may happen no matter how the sock is oriented or positioned within the prosthesis.

In addition or alternative to the embodiments discussed with reference to FIGS. 8A to 8C, a layer of conductive paint may be added within the wall of a prosthetic sock. For example, the conductive paint may include elements of iron, steel, silver, gold, or some other conductive metal, or in some embodiments, elements of non-conductive materials. The conductive paint may advantageously improve the coupling and efficiency between the antenna of a sensor and the antenna associated with a data collection unit.

Further, in addition or alternative to the embodiments discussed with reference to FIGS. 8A to 8C, a resonant circuit or tuned circuit, including, for example, an inductor and a capacitor, may be included within the sock. For example, the circuitry discussed with reference to FIGS. 8A to 8C may include such a resonant circuit or tuned circuit. The circuit may be tuned to a certain frequency so as to uniquely identify the prosthetic sock coupled to the circuit via the unique frequency.

Figure 9:
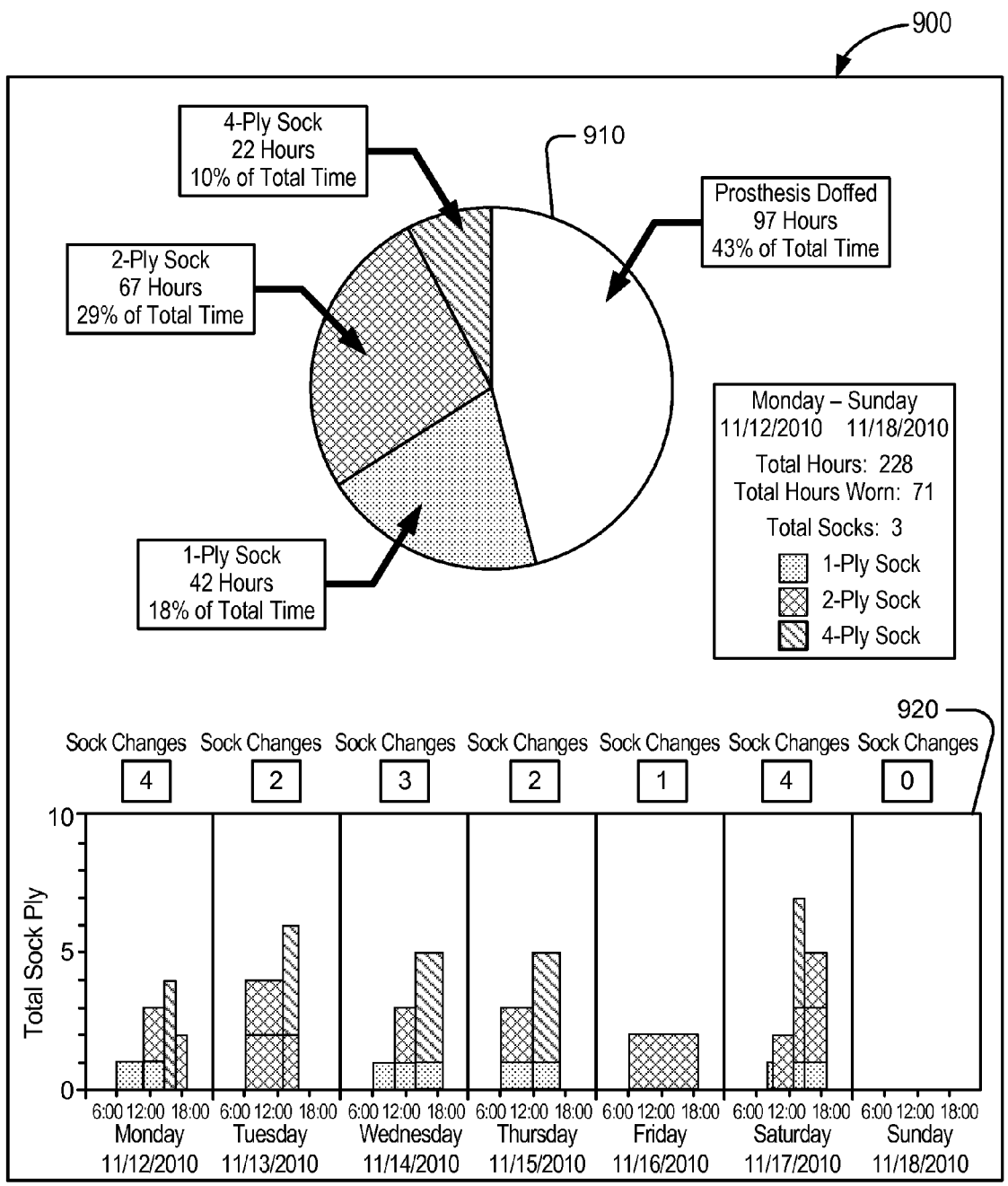
FIG. 9 shows a graphical user interface operable to display data collected and processed by a computing device.

FIG. 9 shows a graphical user interface (GUI) 900 operable to display data collected and processed by a computing device. GUI 900 may be displayed on any suitable computing device, such as mobile computing device 120 and/or remote computing station 130. GUI 900 may be generated by processing information received by data collection unit 111 from one or more sensors 115.

According to this embodiment, GUI 900 displays collected data to the practitioner in a manner that informs clinical decision-making GUI 900 includes both graphical and tabulated data. The pie chart 910 shows sock ply use while the prosthesis is worn. It also shows the actual time of use for each sock thickness. In the lower plot 920, each time a sock ply change is made, the stack of blocks changes. Each color represents a sock ply. Thus from these data, a user can see if a patient is adding socks or changing socks, and when the patient makes those changes. A patient who adds socks only during the first 30 minutes after rising has much different issues than a patient who adds socks four or five times over the course of the day. If a patient is adding socks frequently, the socket may be way too large, and a smaller socket is needed. If many sock ply are added but only very early in the day, this result would indicate the normal situation of much limb volume increase overnight that quickly dissipates the next morning with minor prosthesis use. In the lower plot 920, the sample interval can be adjusted, being changed from 4 hour segments to, e.g., 30 minute segments. This adjustment allows the practitioner to easily discern when and how often ply changes are made.

Figure 10:
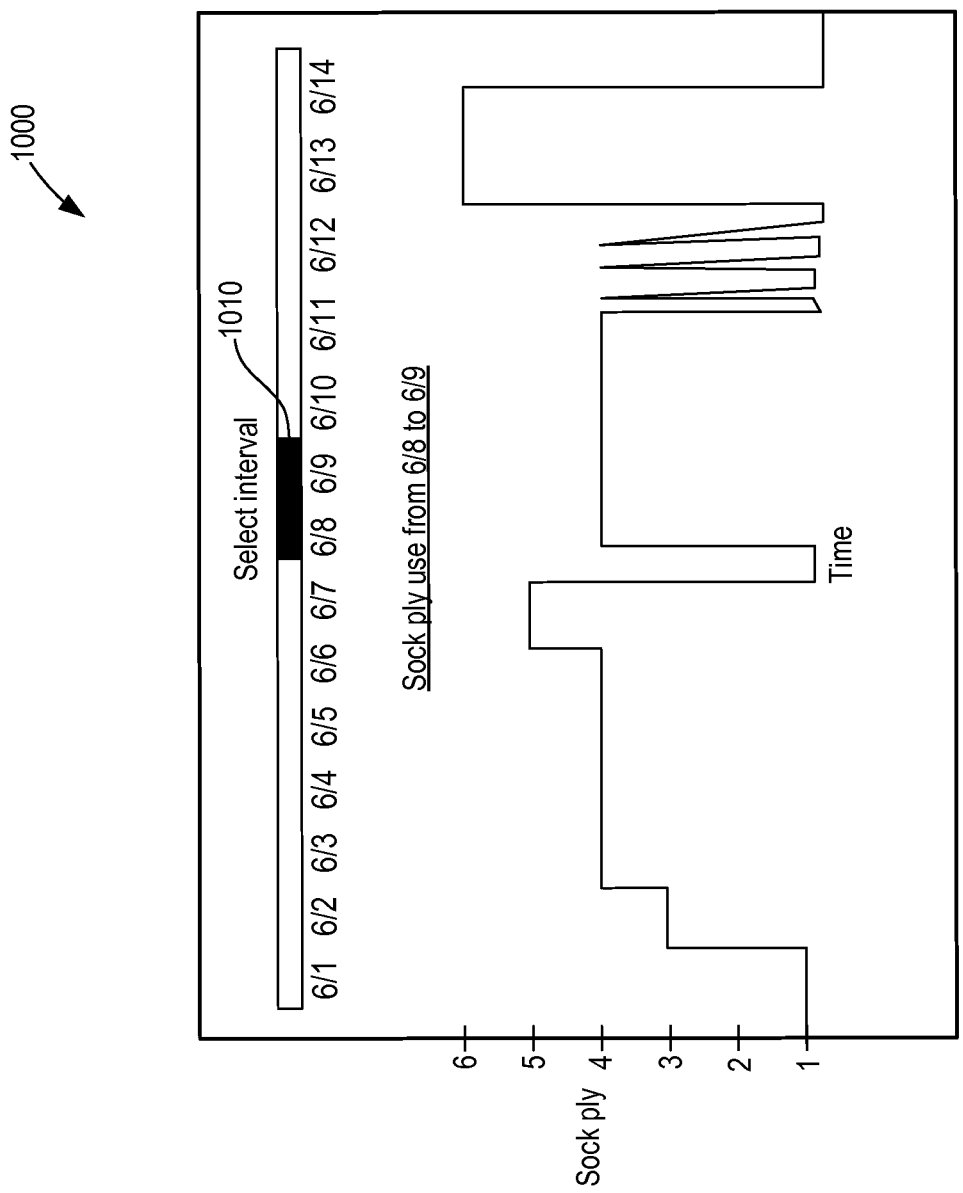
FIG. 10 shows a graphical user interface operable to display data collected and processed by a computing device according to a second embodiment.

FIG. 10 shows a graphical user interface (GUI) 1000 operable to display data collected and processed by a computing device according to a second embodiment. GUI 1000 may be displayed on any suitable computing device, such as mobile computing device 120 and/or remote computing station 130. GUI 1000 may be generated by processing information received by data collection unit 111 from one or more sensors 115.

According to this embodiment, a user can adjust the interval of viewing, via adjustment to the tab 1010, to see multiple days of data, or to zoom in on one particular day or interval. This versatility caters to the user's needs in that the user may be looking for deviations from a regular sock use pattern, as well as excessive sock ply additions outside of the usual early morning interval. In addition the number of sock plys over a time interval, other information may be displayed upon receiving a user selection. For example, GUI 1000 may show the average and standard deviation of the plys, the number of changes over an interval, the length of time a patient wears each ply, etc. This interface can also present force data, or processed force data that indicates if the person is sitting, standing, undergoing cyclic activity, other activity, doffing, etc. This information may help the practitioner identify activities that preclude sock addition Results such as those displayed via GUI 900 and GUI 1000 that may be generated by processing data from a number of different sources according to a first embodiment. For example, sensor information provided by sensors 115 and/or information provided by data collection unit 111 may be received and processed. For another example, self-report surveys may be generated and sent to patients to assess patients' daily comfort and incidences of abrasion, breakdown or other skin conditions (e.g., verrucous hyperplasia) associated with poor fit of a prosthetic socket. The results of such surveys may thus also be received and processed. For another example, patients' practitioners' or other medical technicians (e.g., prosthetists) may submit various information such as specific volume and/or sock management recommendations for the patient. Such information may also be processed. Another use of the collected information is that it informs on how much a particular sock is used. This information may provide insight towards sock replacement programs since socks tend to thin with use. In some embodiments, the unit is programmed so as to monitor total use for each sock, and then inform the patient and/or practitioner when a certain threshold use time has been exceeded.

Figure 14:
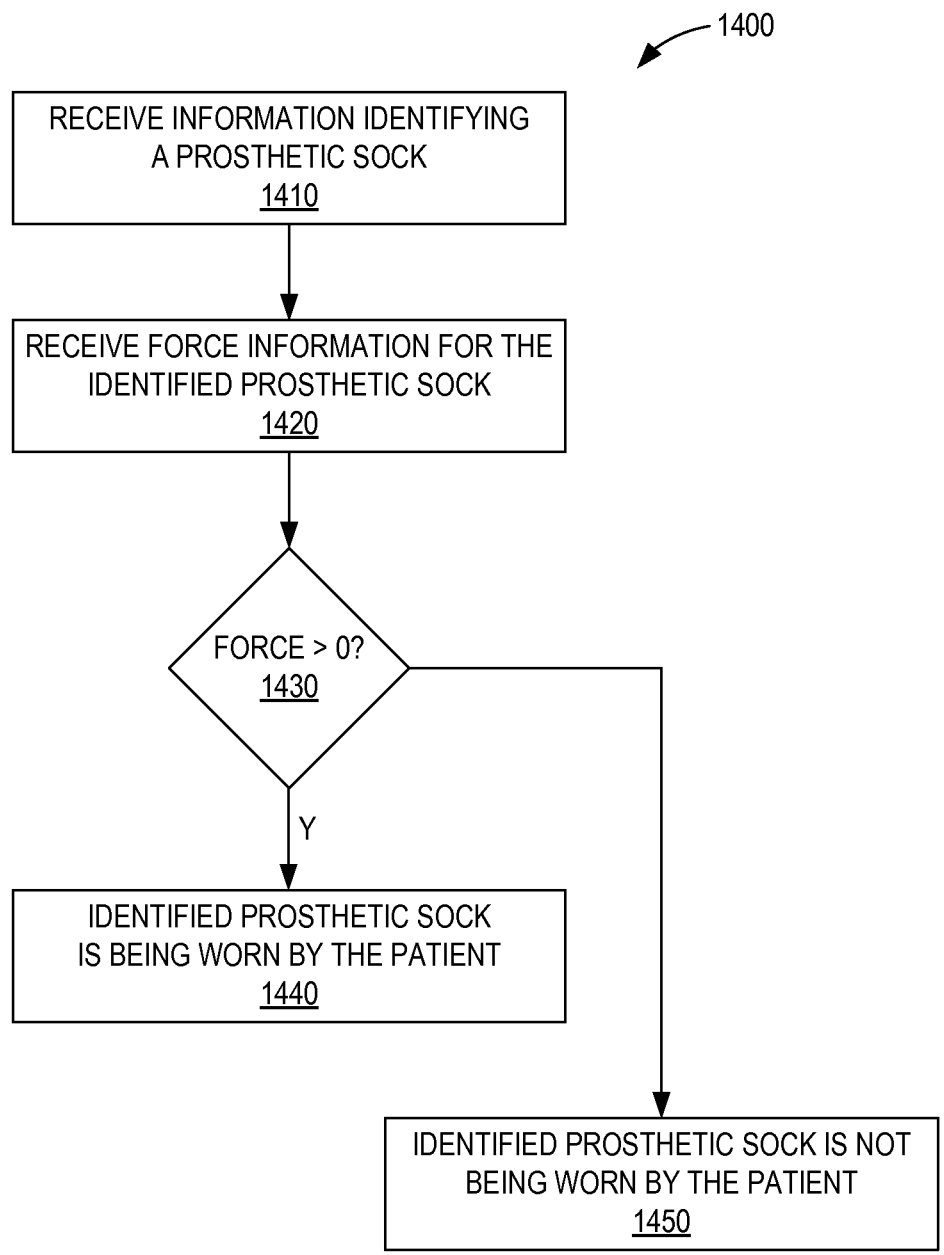
FIG. 14 is a flowchart of a process for determining whether a prosthetic sock is being worn by a patient according to an embodiment of the present invention.

FIG. 14 is a flowchart of a process 1400 for determining whether a prosthetic sock is being worn by a patient according to an embodiment of the present invention. Process 1400 can be performed by any suitable electronic device such as processor 226, but is equally applicable to other electronic devices and accessories described herein.

In operation 1410, processor 226 receives information identifying a prosthetic sock. For example, processor 226 may receive an identifier or other characteristic information from sock identification unit 229a. In operation 1420, processor 226 receives force information for the identified prosthetic sock. For example, processor 226 may receive information from force sensing device 229b that indicates an amount of force applied to the force sensing device located in the same sock as that identified in operation 1410.

In operation 1430, processor 226 determines whether the force applied to the force sensing device located in the sock identified in operation 1410 is equal to zero. If the force is not equal to zero, then processor 226 determines in operation 1440 that the identified prosthetic sock is currently being worn by the patient, since the applied forces are likely to correlate to sock usage. On the other hand, if the force is equal to zero, then processor 226 determines in operation 1450 that the identified prosthetic sock is not currently being worn by the patient, since a lack of forces indicates that the sock is not being moved much less worn by the patient.

In some embodiments, processor 226 may perform additional analysis on received force information to determine or confirm whether an identified sock is actually in use. For example, the processor may read force measurements for a certain period of time, where a force must be measured for at least a predetermined amount of time before processor 226 determines that the sock is being worn by the patient. For another example, one or more force profiles corresponding to sock usage may be stored in storage device 221, and processor 226 may compare received force information to the stored profiles and determine whether the sock is being worn based on the comparison. One skilled in the art will appreciate that another type of sensor, for example a capacitive sensor that detects contact between the sock or liner and prosthesis, could also be used to determine whether the prosthesis is being worn.

In at least one embodiment, processor 226 may perform additional analysis on received force and/or sock data so as to correct for error in the sock data. Sporadic sock detection but continuous non-zero force detection may indicate that the prosthetic socket was not removed and the sock monitor intermittently failed to detect that the sock was present.

Figure 15:
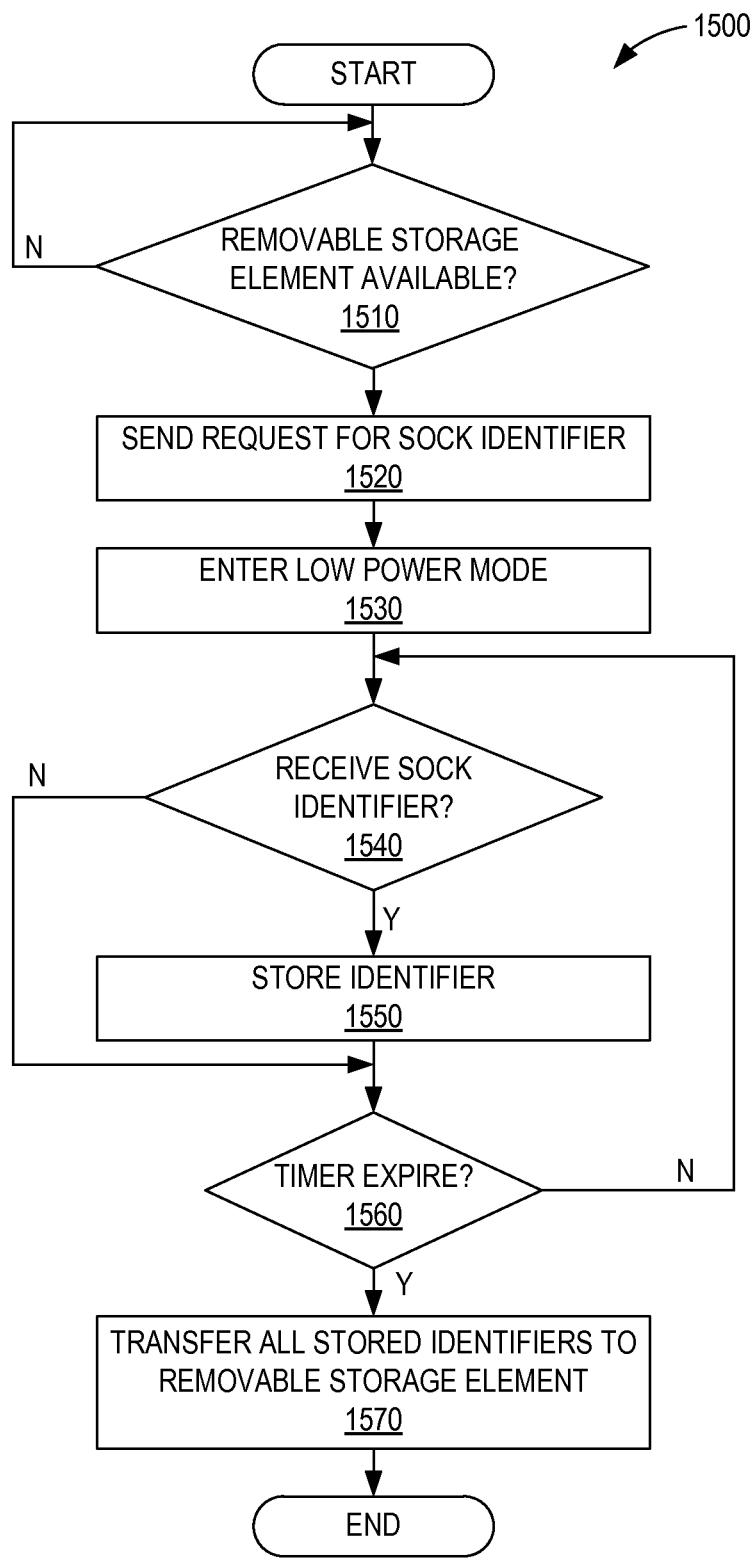
FIG. 15 is a flowchart of a process for storing sock identifiers according to an embodiment of the present invention.

FIG. 15 is a flowchart of a process 1500 for storing sock identifiers according to an embodiment of the present invention. Process 1500 can be performed by any suitable electronic device such as processor 226, but is equally applicable to other electronic devices and accessories described herein.

In operation 1510, processor 226 determines whether a removable storage element (e.g., storage device 221) is available. If not, processing returns to the beginning where the processor again determines whether a removable storage element is available. If so, then in operation 1520, processor 226 sends a request for a sock identifier to sock communication unit 225. In response, sock communication unit 225 may poll the sensors for a sock identifier. In operation 1530, processor 226 may cause data collection unit 220 to enter a low power mode, such as that discussed with reference to FIG. 16. In operation 1540, processor 226 determines whether a sock identifier is received. If a sock identifier is received, in operation 1550 processor 226 may store the sock identifier in temporary memory either in or coupled to processor 226. If a sock identifier is not received, processing may continue to operation 1560.

In operation 1560, processor 226 determines whether a timer has expired. The timer may begin, for example, after entering low power mode. If the timer has not expired, processing may return to operation 1540. If the timer has expired, processing may continue to operation 1570 where processor 226 transfers all sock identifiers stored in temporary memory to the removable storage element (e.g., storage device 221). By performing such a data transfer technique, sock identifiers may reliably be backed up while power consumption is minimized.

One of ordinary skill in the art would recognize that embodiments are not limited to the detection and storing of sock identifiers, but may be suitable for receiving and storing a variety of types of information. For example, this process may be used to receive and store any of the information discussed herein that may be provided by sock identification unit 229a, and/or force sensing device 229b. Further, one of ordinary skill in the art would recognize that embodiments are not limited to techniques concerning removable storage devices, but may equally be applicable to techniques using non-removable storage elements. For example, in operation 1510, it may be determined whether a non-removable storage element is available.

Figure 16:
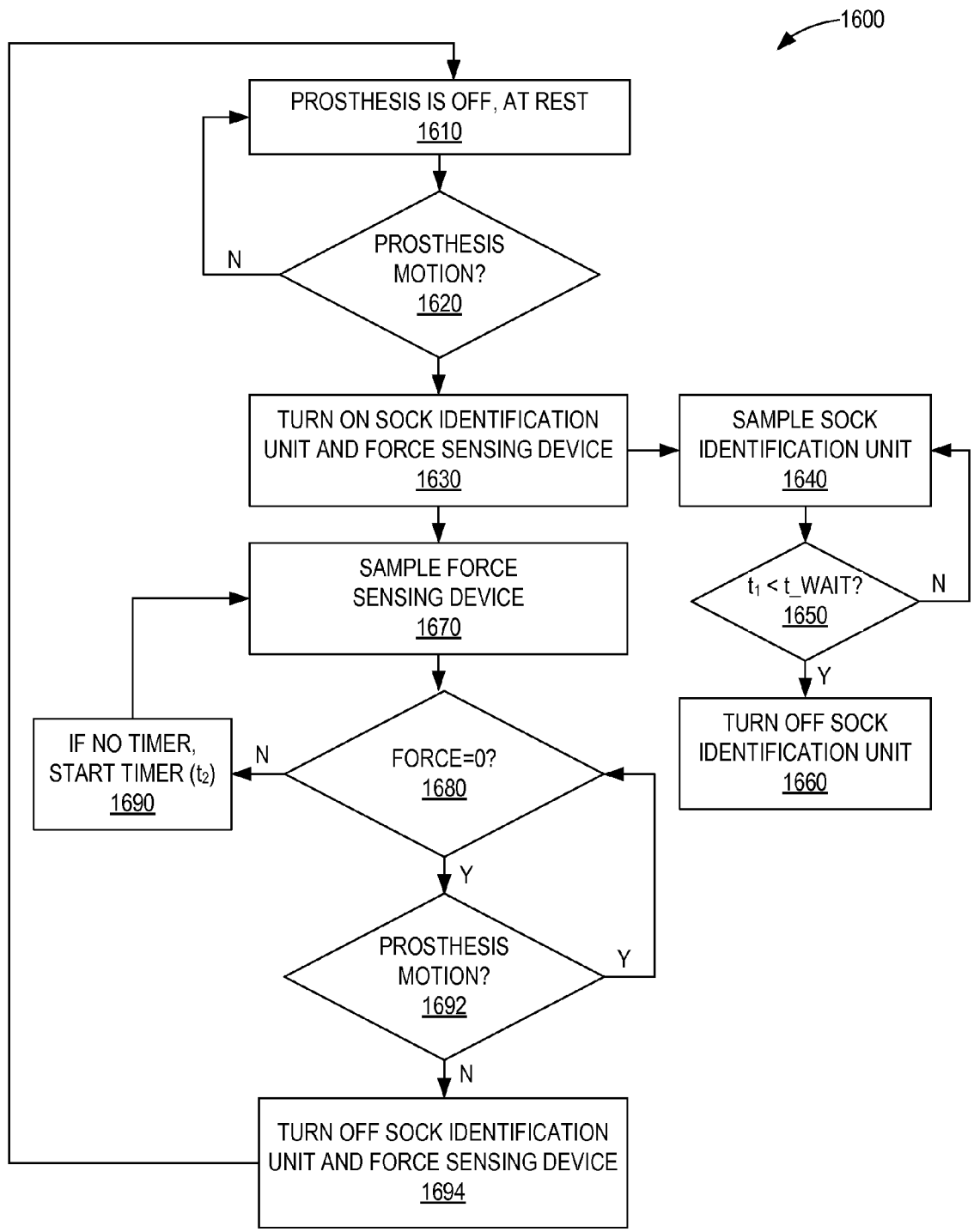
FIG. 16 is a flowchart of a process for acquiring information from sensors such as sock identifiers and force sensing devices while preserving power according to an embodiment of the present invention.

FIG. 16 is a flowchart of a process 1600 for acquiring information from sensors such as sock identifiers and force sensing devices while preserving power according to an embodiment of the present invention. Process 1600 can be performed by any suitable electronic device such as processor 226, but is equally applicable to other electronic devices and accessories described herein.

In operation 1610, the prosthesis 112 is not worn by a patient and is at rest. In operation 1620, processor 226 determines whether the prosthesis 112 is in motion. For example, motion sensing device 222 may be coupled to the prosthesis, and processor 226 may receive information from motion sensing device 222 indicating movement of the prosthesis. For another example, force sensing device 229b may be active and indicate a change in force applied to the force sensing device 229b. Accordingly, donning and/or doffing of the prosthesis 112 can be detected, and subsequent processing (e.g., sock identification) performed immediately after it is determined that the prosthesis 112 is in motion (e.g., being donned or doffed). If processor 226 determines that the prosthesis is not in motion, then processing returns to operation 1610 where the prosthesis is off and at rest. Otherwise, processing continues to operation 1630.

In operation 1630, processor 226 turns on one or more sensors, such as sock identification unit 229a and/or force sensing device 229b. By turning on the sensors, processor 226 may instruct any sensors in range to turn on. Additionally or alternatively, processor 226 may cause data collection unit 220 to remotely power these sensors. In some embodiments, one or more sensors may be activated only for a certain period of time after detecting motion of the prosthesis. For example, the sock identification unit 229a may be activated for a certain period of time (e.g., 5 seconds, 10 seconds, 30 seconds, in a range from 5 seconds to 30 seconds, for a time less than 5 seconds or greater than 30 seconds) after determining that prosthesis 112 is in motion. In another embodiment, the sock identification unit 229 may be activated until the force sensing device or another device detects that the residual limb is within the prosthetic socket. This may advantageously result in greater detection of sock identifiers as some wireless identification systems (e.g., RFID systems) often have better detection accuracy for tags that are in motion rather than at a standstill relative to the reader.

In operation 1640, processor 226 samples the sock identification unit 229a. For example, processor 226 may instruct sock communication unit 225 to poll for any sock identification units in range, and store any information received from the sock identification units. In operation 1650, processor 226 determines whether a timer (t1) is less than an amount of time (twait). If not, processing returns to operation 1640. Otherwise, processing continues to operation 1660, where the sock identification unit is turned off. For example, data collection unit may instruct sock identification unit 229a to turn off, or may stop providing power to sock identification unit.

In operation 1670, processor 226 samples force sensing device 229b. For example, processor 226 may instruct sock communication unit 225 to poll for any force sensing devices in range, and receive and process any information received from the force sensing devices. In operation 1680, the processor 226 determines whether the information received indicates that the force applied to the force sensing device is equal to zero. If it is not, then processing continues to operation 1690, where if no timer is set, the timer (t1) is set. Otherwise, processing continues to operation 1692.

In operation 1692, the processor 226 determines whether the prosthesis is in motion, similar to operation 1620. If so, then processing returns to operation 1680. If not, processing continues to operation 1694. In operation 1694, the sock identification unit and force sensing devices are turned off. For example, data collection unit 220 may communicate signals to sock identification unit 229a and force sensing device 229b to turn off, or may stop powering those devices. Processing may then return to operation 1610.

It should be appreciated that the specific operations illustrated in FIGS. 14 to 16 provide particular methods that may be executed by a computing device, such as data collection unit 220, mobile computing device 240, and/or remote computing station 250, according to certain embodiments of the present invention. While the operations illustrated in FIGS. 14 to 16 are often discussed with reference to FIG. 2, it should be appreciated that the operations may be performed by other described herein, such as those described with reference to FIG. 1. Further, other sequences of operations may also be performed according to alternative embodiments. For example, alternative embodiments of the present invention may perform the operations outlined above in a different order. Moreover, the individual operations illustrated in FIGS. 14 to 16 may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives.

Experimental Data

A test subject was used to evaluate the prosthetic sock monitoring system using a series of tests that would put the prosthesis through ranges of motion that would be experienced in everyday use outside the lab.

Three tags were placed on the subjects sock to evaluate where the best placement of the tags should be. The edge of the first tag was placed approximately 5 cm from the most distal end of the subjects limb, the edge of the second tag was placed approximately 3 cm from the edge of the previous tag and the edge of the third tag was placed approximately 4 cm from the edge of the second tag. The device was placed on a subject's prosthesis while the subject puts their limb through various ranges of motion, including donning and doffing of the prosthesis, squatting, elevating the prosthesis, walking on a treadmill, walking up and down stairs, stuffing socks into the socket of the prosthesis, and jumping.

The subject used an endoskeletal total surface bearing carbon fiber socket. The subject wore an Alps 3 mm gel liner, size 24. Over the Alps liner, the subject wore a cotton 1 ply sock where 3 tags were attached. Over the sock and liner, the subject wore a flexible polyethylene liner with a pin that connects into a one way valve in the socket.

Figure 12:
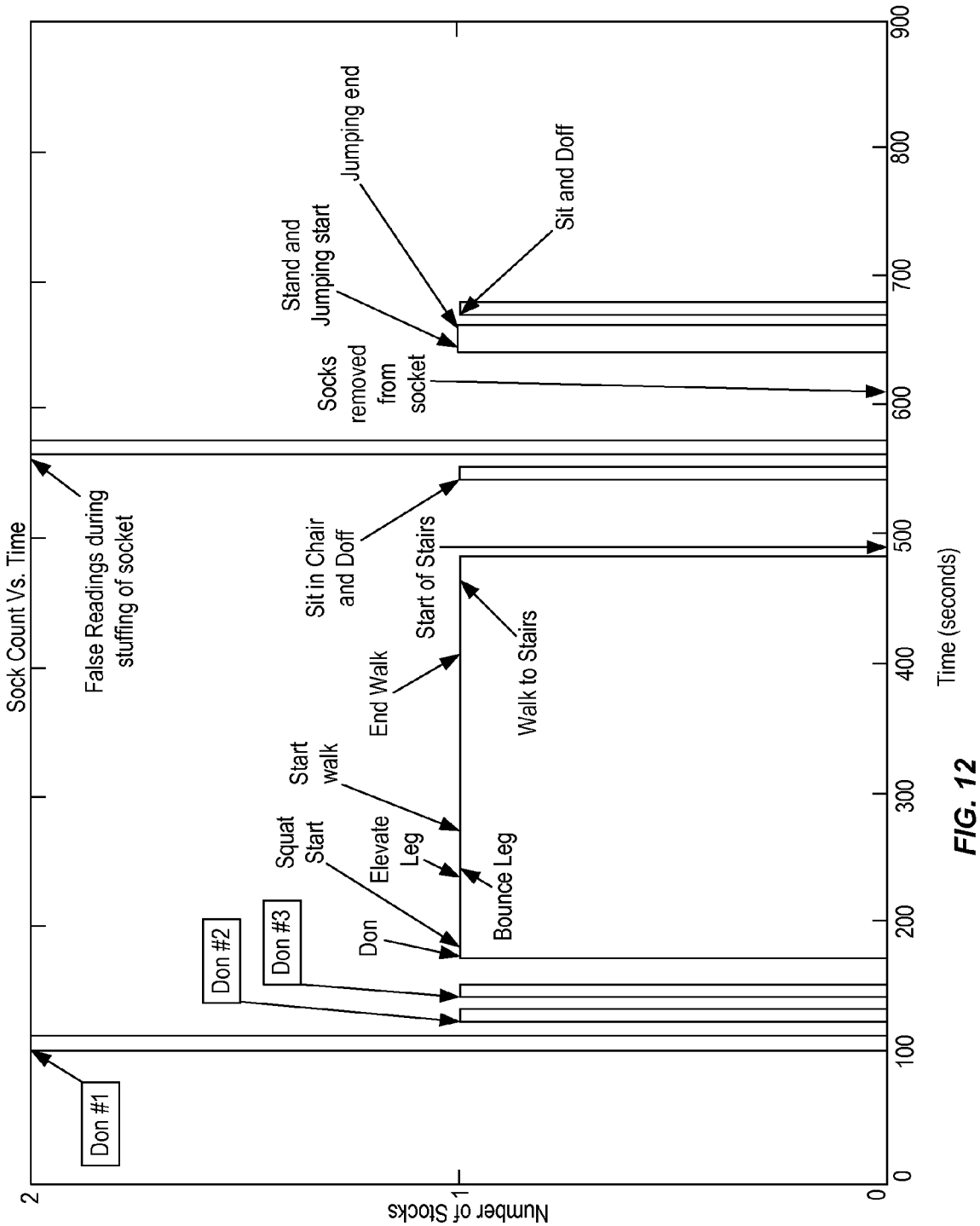
FIG. 12 illustrates the results of the patient testing including the number of socks over time correlated with patient activity.

Results. Sock Count. FIG. 12 illustrates the results of the testing including the number of socks over time correlated with patient activity. During the test, only one tag was detected except during two scan windows. Two tags were detected first during the first donning, the second two-tag detection was during the sock stuffing test. There were also two errors during the test, meaning that there was no data collected when there should have been or there was data collected when there should not have been. The first error occurred when there was a drop out in the tag detection after the treadmill but before the stairs test. No tags were detected until the subject returned to the lab and doffed their prosthesis. Just prior to doffing the system detected a tag. The second error occurred when the subject stuffed their socks into the empty socket. The system detected two of three tags during the first scanning window of the stuffing test. However, after this first scan, the system no longer detected the tags attached to the subject's socks. Further, when reviewing the data, there were times when the RFID system seemed to not detect the presence of a tag when first inserted or it would detect a tag that was missing right after the tag's removal from the socket. This "error" was in fact caused by the tag just missing or being just inside of the 10 second detection window.

Figure 13:
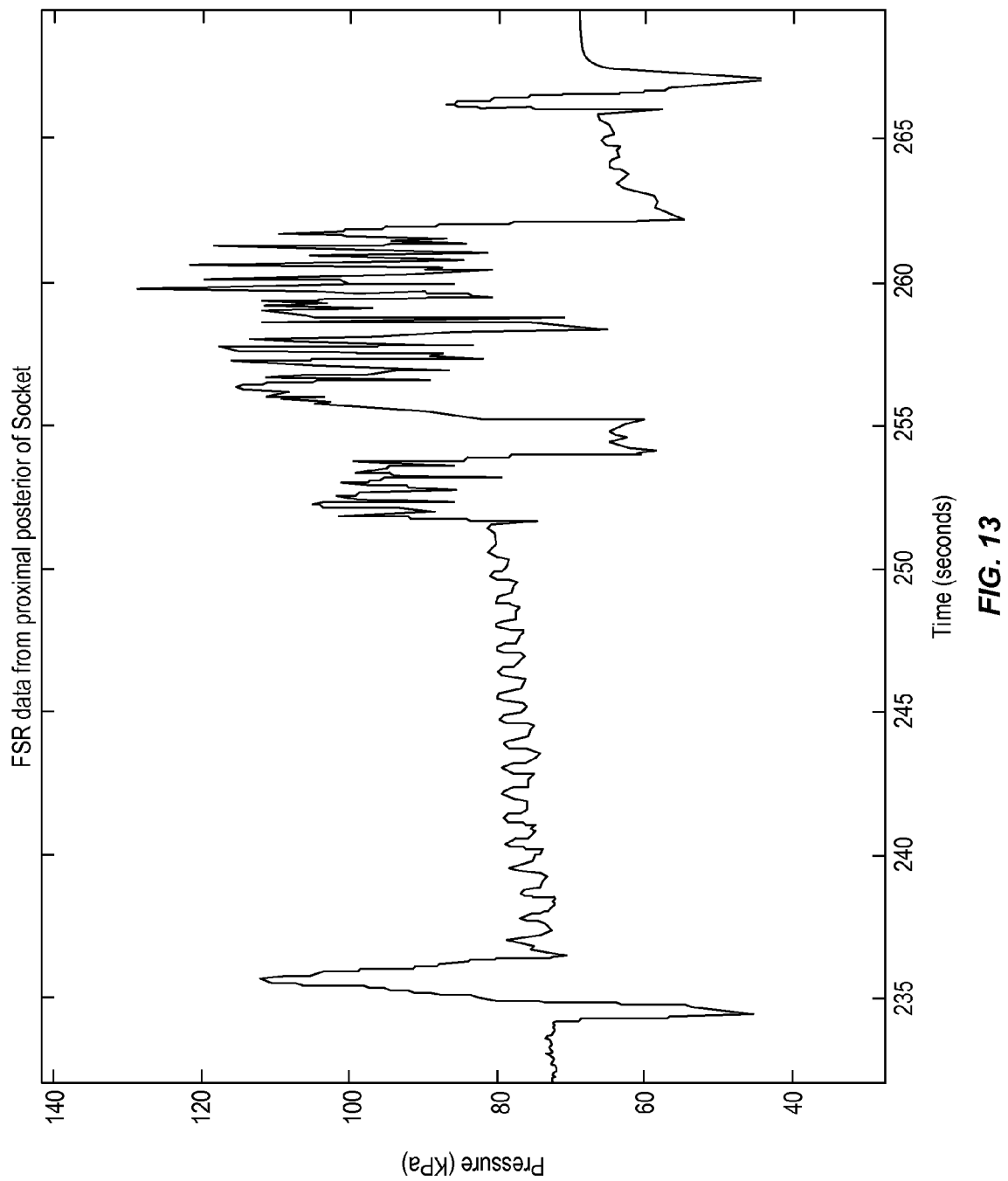
FIG. 13 illustrates the results of the patient testing including pressure data over time.

Force Sensing Device Data. The device successfully recorded continuous force sensing device data during the entirety of the test. There was nothing unusual about the data except during the elevated leg test. While the subject was resting their prosthesis on a chair and holding still, small 1-1.5 cycle per second oscillations were observed with an amplitude of around 4-5 kPa. FIG. 13 shows these results including pressure data over time. These results are particularly surprising in that they indicate that a force sensing device such as a force sensing resistor located in a prosthetic sock is particularly sensitive, even moreso than equivalent force sensing devices located in an elastomeric liner, and in some cases is sensitive enough to monitor a patient's heartbeat.

The software components or functions described in this application may be implemented as software code to be executed by one or more processors using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may also reside on or within a single computational apparatus, and may be present on or within different computational apparatuses within a system or network.

The present invention can be implemented in the form of control logic in software or hardware or a combination of both. The control logic may be stored in an information storage medium as a plurality of instructions adapted to direct an information processing device to perform a set of steps disclosed in embodiments of the present invention. Based on the disclosure and teachings provided herein, a person of ordinary skill in the art will appreciate other ways and/or methods to implement the present invention.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Preferred embodiments are described herein, including the best mode known to the inventors. Variations of those preferred embodiments may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

What is claimed is:

1. A prosthetic sock for disposition over residual limb of a patient and insertion into a socket of a prosthesis associated with the patient, the prosthetic sock comprising:
   material shaped to fit over at least a portion of the residual limb of the patient and of a thickness adapted for inserting the residual limb into the socket of the prosthesis while the sock is fitted over the residual limb;
   a sock identification unit operable to identify at least one identifying characteristic of the prosthetic sock and communicate the at least one identifying characteristic to a computing device separate from the prosthetic sock, the at least one identifying characteristic being configured to distinguish the prosthetic sock from other prosthetic socks; and
   a force sensing device operable to determine an amount of force applied to the force sensing device and communicate information indicating the amount of force applied to the force sensing device to the computing device separate from the prosthetic sock, and wherein the sock identification unit and the force sensing device are integrated into a single device;
   wherein one or more of the sock identification unit and the force sensing device are provided at a predetermined location on or in the material, the predetermined location being associated with the placement of an antenna located in the socket of the prosthesis.

2. The prosthetic sock of claim 1, wherein the sock identification unit is selected from the group consisting of: a passive radio frequency identification tag, and an active radio frequency identification tag.

3. The prosthetic sock of claim 1, wherein the force sensing device is selected from the group consisting of: a piezoelectric sensor, a piezoresistive film sensor, a capacitive film sensor, and an optical pressure sensor.

4. The prosthetic sock of claim 1, wherein one or more of the sock identification unit and the force sensing device are operable to communicate information to the computing device using a frequency band selected from the group consisting of: very low frequency, low frequency, medium frequency, high frequency, very high frequency, ultra high frequency, super high frequency, extremely high frequency, and tremendously high frequency.

5. The prosthetic sock of claim 1, wherein one or more of the sock identification unit and the force sensing device are located at a brim of the material, an end of the material opposite an end for receiving the residual limb of the patient, and a location corresponding to a center of the antenna when the prosthetic sock is disposed over the patient's residual limb and inserted into the socket of the prosthesis.

6. The prosthetic sock of claim 1, wherein one or more of the sock identification unit and the force sensing device include a transmission antenna having an orientation such that, when the prosthetic sock is disposed over the patient's residual limb and inserted into the socket of the prosthesis, the transmission antenna is arranged in parallel with the antenna located in the socket of the prosthesis.

7. The prosthetic sock of claim 1, further comprising an additional sensor operable to sense one or more of displacement between a region of the material and the socket, temperature of a region of the material, oxygen saturation, pulse, blood flow, and angle of the socket.

8. The prosthetic sock of claim 1, wherein the at least one physical characteristic of the prosthetic sock further comprises at least a sock thickness.

9. The prosthetic sock of claim 1, wherein the at least one physical characteristic of the prosthetic sock further comprises at least a sock ply.

10. The prosthetic sock of claim 1, further comprising a sensor operable to determine at least two use cases, the at least two use cases comprising:
    whether the prosthetic sock is being worn; and
    whether the prosthetic sock is being worn in combination with a prosthesis.

11. The prosthetic sock of claim 10, wherein the at least two use cases further comprise:
    whether the prosthetic sock is being worn in combination with one or more additional prosthetic socks.

12. The prosthetic sock of claim 1, further comprising a displacement sensor configured for measuring a distance between the prosthetic sock and a socket.

13. A mobile computing device associated with a patient having a residual limb onto which the patient is capable of disposing a prosthetic sock for insertion into a socket of a prosthesis associated with the patient, the mobile computing device comprising:
    a storage element for receiving information defining a sock management strategy;
    a processor for processing the information defining the sock management strategy to determine when the patient should wear the particular prosthetic sock selected from the plurality of different prosthetic socks; and
    an output device for providing an indication to the patient indicating when the patient should wear the particular prosthetic sock selected from the plurality of different prosthetic socks.

14. The mobile computing device of claim 13, wherein the indication is selected from the group consisting of: an auditory indicator, a visual indicator, and a tactile indicator.

15. The mobile computing device of claim 13, further comprising:
    a communication unit operable to receive information communicated from a data collection unit associated with the patient.

16. The mobile computing device of claim 15, wherein the information communicated from the prosthetic sock monitoring system includes information identifying at least one characteristic of a prosthetic sock currently being worn by the patient, and the processor is operable to determine when the patient should wear a particular prosthetic sock based on the sock currently being worn by the patient.

17. The mobile computing device of claim 15, wherein the information communicated from the prosthetic sock monitoring system includes information indicating the amount of force applied to a force sensing device coupled to a prosthetic sock currently being worn by the patient, and the processor is operable to determine when the patient should wear a particular prosthetic sock based on the amount of force applied to the force sensing device.

18. A prosthetic sock for disposition over residual limb of a patient and insertion into a socket of prosthesis associated with the patient, the prosthetic sock comprising:
material shaped to fit over at least a portion of the residual limb of the patient and of a thickness adapted for inserting the residual limb into the socket of the prosthesis while the sock is fitted over the residual limb; and
one or more displacement sensors operable for determining at least a distance between the prosthetic sock and the socket.

19. The prosthetic sock of claim 18, wherein the one or more displacement sensors are further operable to communicate the at least the distance to a computing device separate from the prosthetic sock.

20. The prosthetic sock of claim 18, wherein the sensor is provided at a predetermined location on or in the material, the predetermined location being associated with the placement of an antenna located in the socket of the prosthesis.

21. The prosthetic sock of claim 18, wherein at least one of the one or more displacement sensors is coupled to an interior surface of the prosthetic sock and operable for determining at least a distance between the interior surface of the prosthetic sock and the socket.

22. The prosthetic sock of claim 18, wherein the one or more displacement sensors are embedded within the prosthetic sock.

23. The prosthetic sock of claim 18, wherein at least one of the one or more displacement sensors is coupled to an exterior surface of the prosthetic sock and operable for determining at least a distance between the exterior surface of the prosthetic sock and the socket.

* * * * *